US005700272A

United States Patent [19]
Gordon et al.

[11] Patent Number: 5,700,272
[45] Date of Patent: *Dec. 23, 1997

[54] ENDOSCOPIC SUTURE SYSTEM

[75] Inventors: Norman S. Gordon, Irvine; Robert P. Cooper, Yorba Linda; Richard L. Quick, Trabuco Canyon, all of Calif.

[73] Assignee: Laurus Medical Corporation, Irvine, Calif.

[*] Notice: The term of this patent shall not extend beyond the expiration date of Pat. No. 5,364,408.

[21] Appl. No.: 534,501

[22] Filed: Sep. 27, 1995

Related U.S. Application Data

[60] Division of Ser. No. 57,699, May 4, 1993, Pat. No. 5,458,609, which is a continuation-in-part of Ser. No. 941,382, Sep. 4, 1992, Pat. No. 5,364,408.

[51] Int. Cl.⁶ .................................................. A61B 17/00
[52] U.S. Cl. ........................... 606/144; 606/139; 606/147; 117/169
[58] Field of Search .................................. 606/139, 144, 606/145, 147, 148, 185, 222–227, 186, 187; 604/278; 112/80.03, 169

[56] References Cited

U.S. PATENT DOCUMENTS

| 342,773 | 6/1886 | Bailey . |
|---|---|---|
| 919,138 | 4/1909 | Drake et al. . |
| 1,037,864 | 9/1912 | Carlson et al. . |
| 1,449,087 | 3/1923 | Bugbee . |
| 1,815,725 | 7/1931 | Pilling et al. . |
| 1,822,330 | 9/1931 | Ainslie . |
| 2,577,240 | 12/1951 | Findley . |
| 2,579,192 | 12/1951 | Kohl . |
| 3,013,559 | 12/1961 | Thomas . |
| 3,160,157 | 12/1964 | Chisman . |
| 3,470,875 | 10/1969 | Johnson . |
| 3,638,653 | 2/1972 | Berry . |
| 3,840,017 | 10/1974 | Violante . |
| 3,918,455 | 11/1975 | Coplan . |
| 3,946,740 | 3/1976 | Bassett . |
| 4,161,951 | 7/1979 | Scanlan, Jr. . |
| 4,164,225 | 8/1979 | Johnson et al. . |

(List continued on next page.)

FOREIGN PATENT DOCUMENTS

| 647813 | 9/1962 | Canada . |
|---|---|---|
| 0 140 557 | 5/1985 | European Pat. Off. . |
| 0 589 409 | 3/1994 | European Pat. Off. . |
| 1028320 | 7/1983 | U.S.S.R. . |
| 1093329 | 5/1984 | U.S.S.R. . |
| 18602 | 9/1909 | United Kingdom . |
| 2 247 841 | 3/1992 | United Kingdom . |
| WO90/03766 | 4/1990 | WIPO . |
| WO92/12674 | 8/1992 | WIPO . |
| WO93/01750 | 2/1993 | WIPO . |

OTHER PUBLICATIONS

Description of "Rema Deep Suture", publication status and dates unknown, original document in German, English translation attached.

Primary Examiner—Jeffrey A. Schmidt
Attorney, Agent, or Firm—Dennis H. Epperson

[57] ABSTRACT

A method and device for the placement of sutures and for the purpose of approximating tissue. A particular utility is effected in the approximation of the tissue separated by means of an endosurgical trocar being inserted into a body cavity. The invention provides for the loading of suture material including needles into the device, introduction and placement of the device into the body cavity, with the distal end having deployable needle guides, extending the needle guides either simultaneously or individually to the periphery of the wound, engaging the wound with the needle guides, driving the needles and suture material through the tissue to be approximated into a catch mechanism, retracting the needle guides and withdrawing the device, leaving a loop of suture material in the margin of tissue. The suture may then be tied to approximate the wound and excess suture material cut off.

9 Claims, 26 Drawing Sheets

U.S. PATENT DOCUMENTS

| | | |
|---|---|---|
| 4,224,947 | 9/1980 | Fukuda . |
| 4,235,177 | 11/1980 | Arbuckle . |
| 4,236,470 | 12/1980 | Stenson . |
| 4,312,337 | 1/1982 | Donohue . |
| 4,345,601 | 8/1982 | Fukuda . |
| 4,493,323 | 1/1985 | Albright et al. . |
| 4,548,202 | 10/1985 | Duncan . |
| 4,557,265 | 12/1985 | Andersson . |
| 4,596,249 | 6/1986 | Freda et al. . |
| 4,602,635 | 7/1986 | Mulhollan et al. . |
| 4,621,640 | 11/1986 | Mulhollan et al. . |
| 4,635,638 | 1/1987 | Weintraub et al. . |
| 4,781,190 | 11/1988 | Lee . |
| 4,890,615 | 1/1990 | Caspari et al. . |
| 4,898,155 | 2/1990 | Ovil et al. . |
| 4,899,746 | 2/1990 | Brunk . |
| 4,923,461 | 5/1990 | Caspari et al. . |
| 4,926,860 | 5/1990 | Stice et al. . |
| 4,935,027 | 6/1990 | Yoon . |
| 4,957,498 | 9/1990 | Caspari et al. . |
| 5,037,433 | 8/1991 | Wilk et al. . |
| 5,047,039 | 9/1991 | Avant et al. . |
| 5,067,957 | 11/1991 | Jervis . |
| 5,100,415 | 3/1992 | Hayhurst . |
| 5,100,418 | 3/1992 | Yoon et al. . |
| 5,100,421 | 3/1992 | Christoudias . |
| 5,188,636 | 2/1993 | Fedotov . |
| 5,258,011 | 11/1993 | Drews . |
| 5,306,281 | 4/1994 | Beurrier . |
| 5,308,353 | 5/1994 | Beurrier . |
| 5,387,221 | 2/1995 | Bisgaard . |
| 5,389,103 | 2/1995 | Melzer et al. . |
| 5,391,174 | 2/1995 | Weston . |
| 5,417,699 | 5/1995 | Klein et al. . |
| 5,527,321 | 6/1996 | Hinchliffe . |

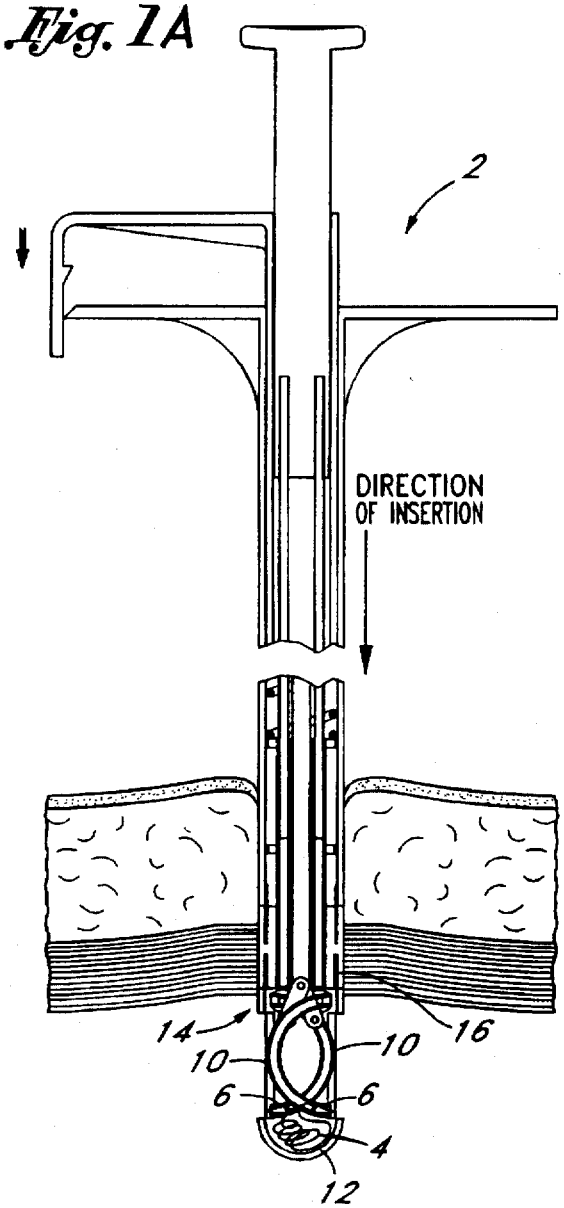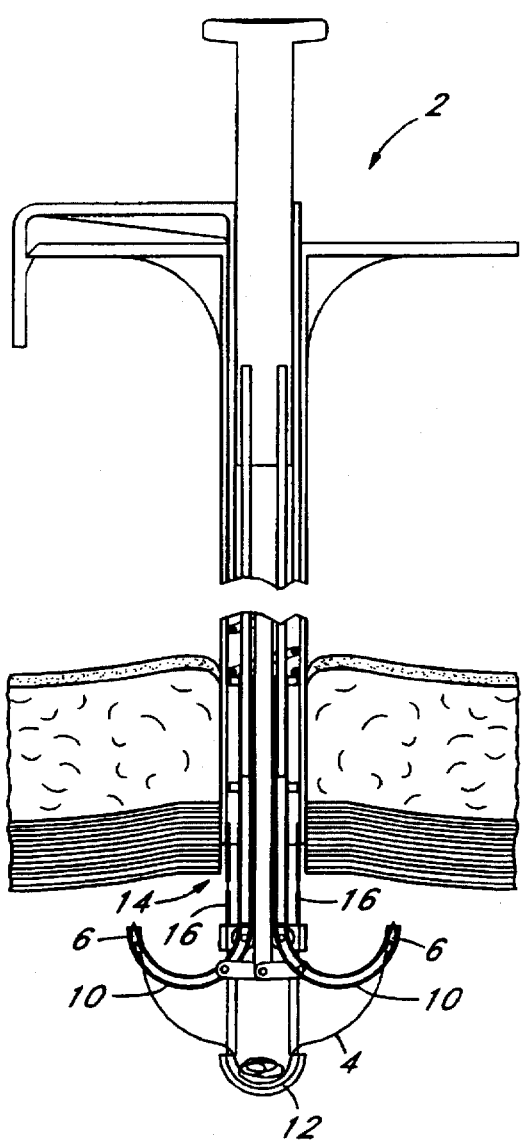

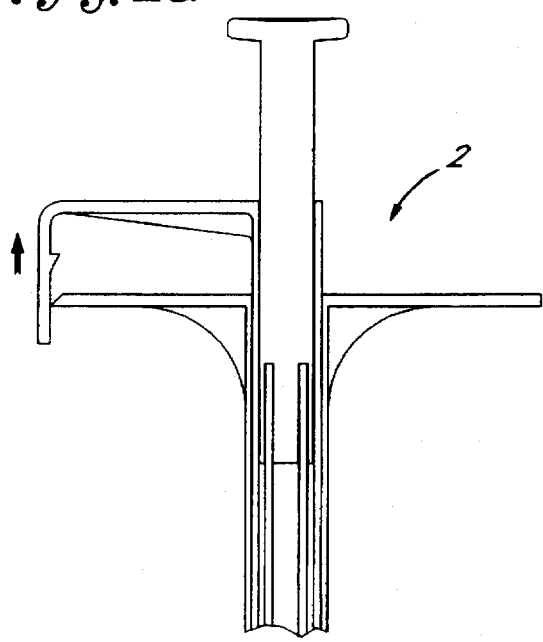
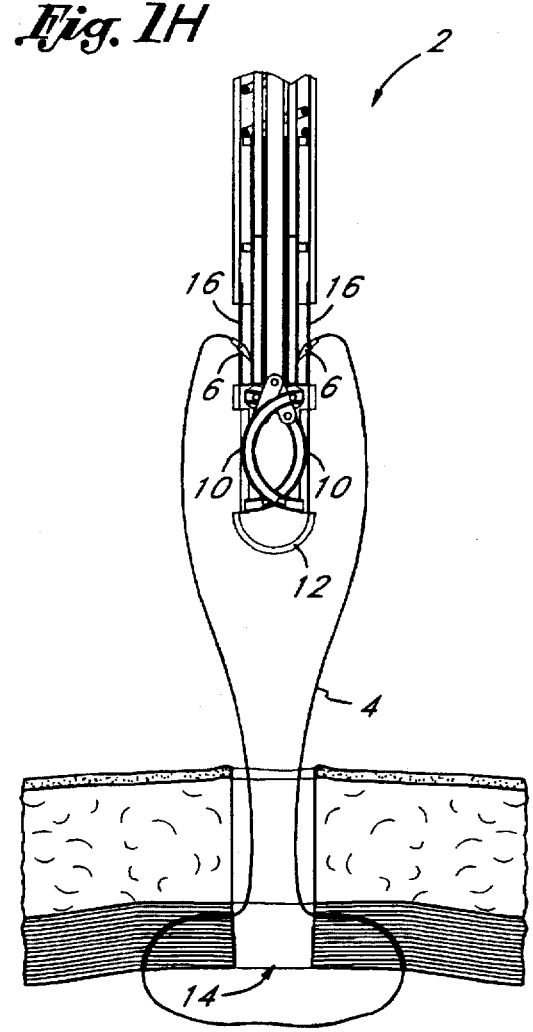
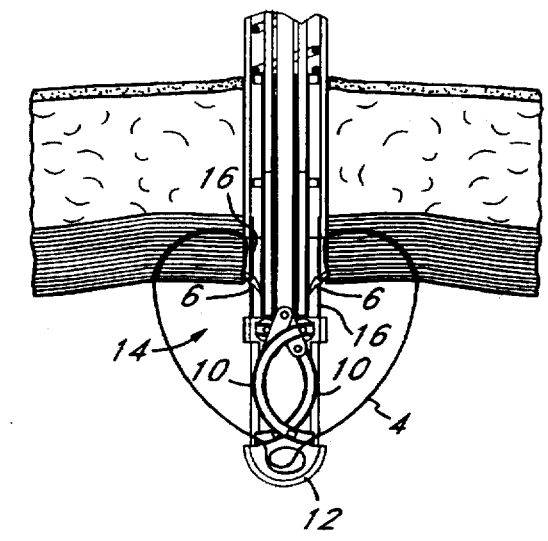
Fig. 1G  Fig. 1H

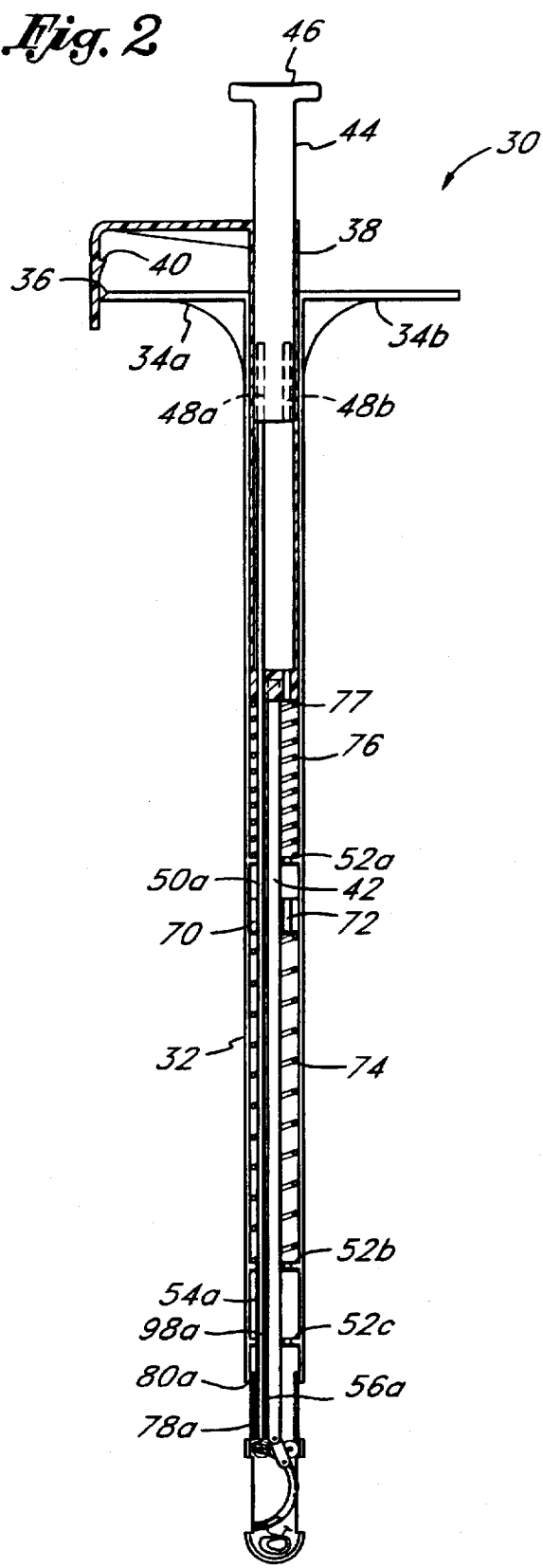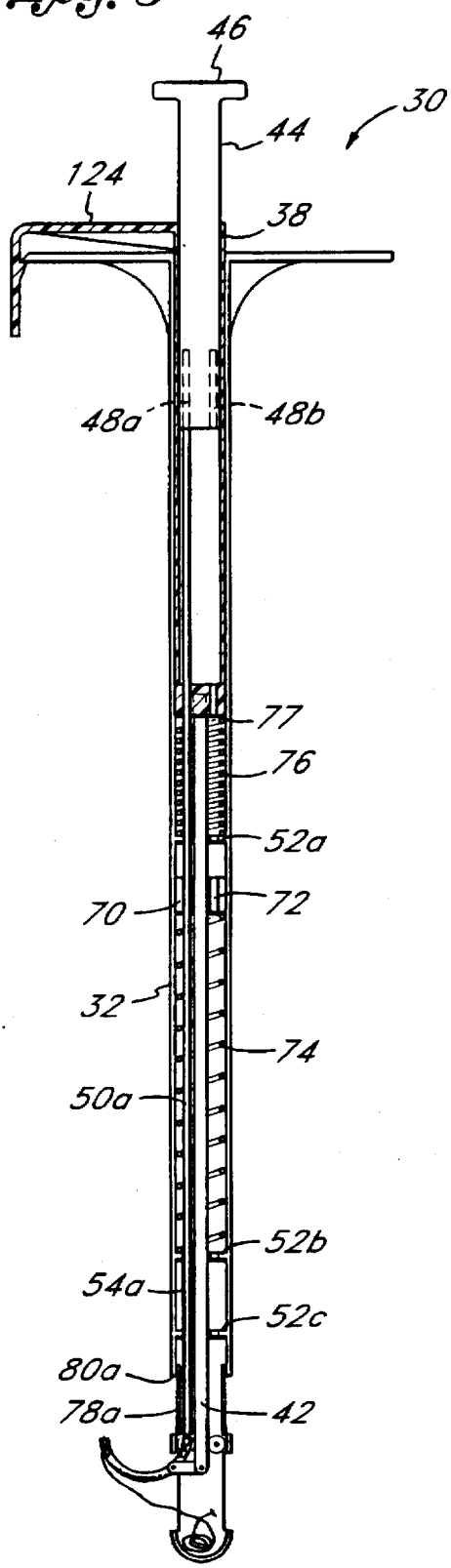

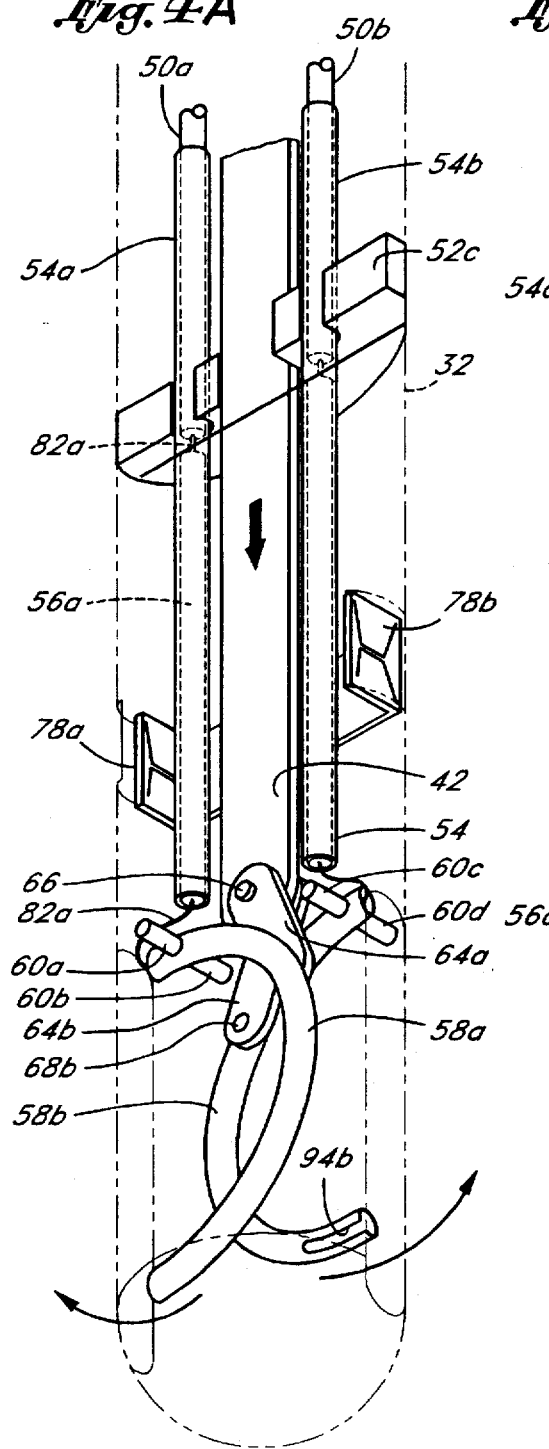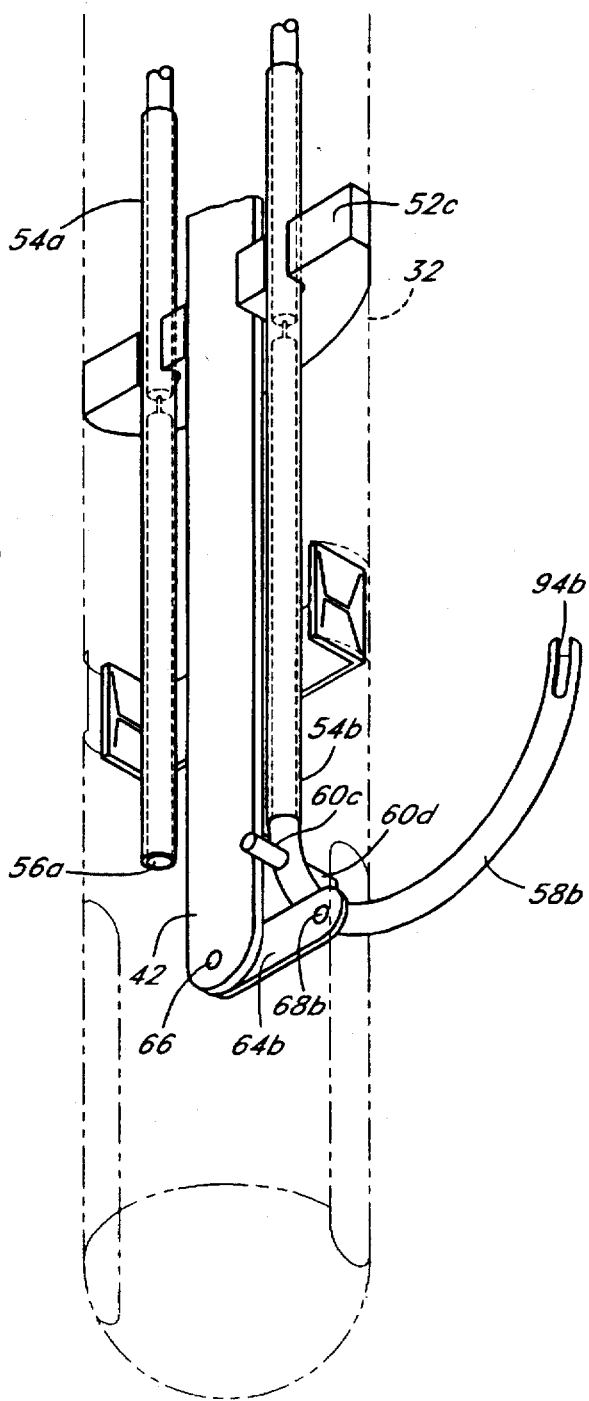

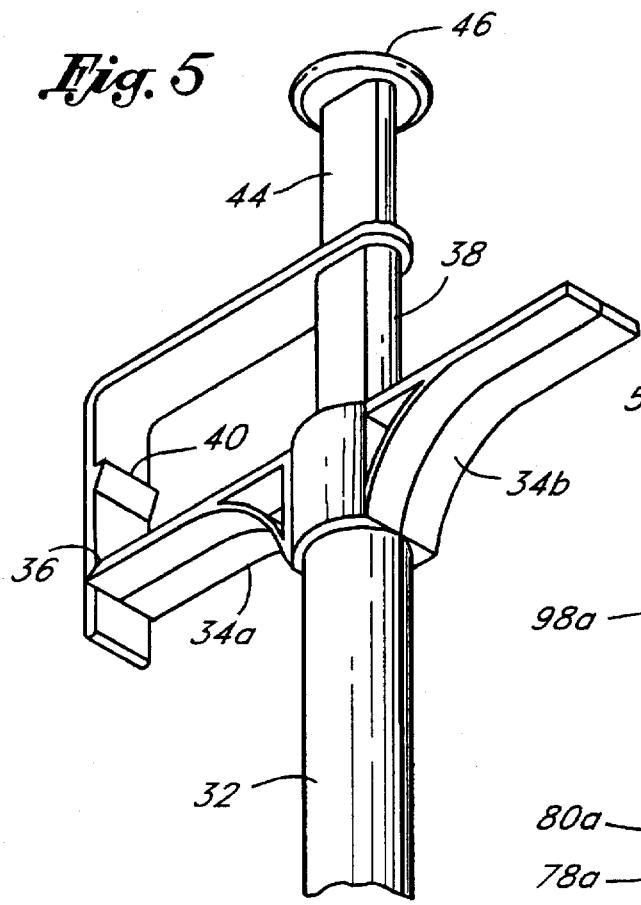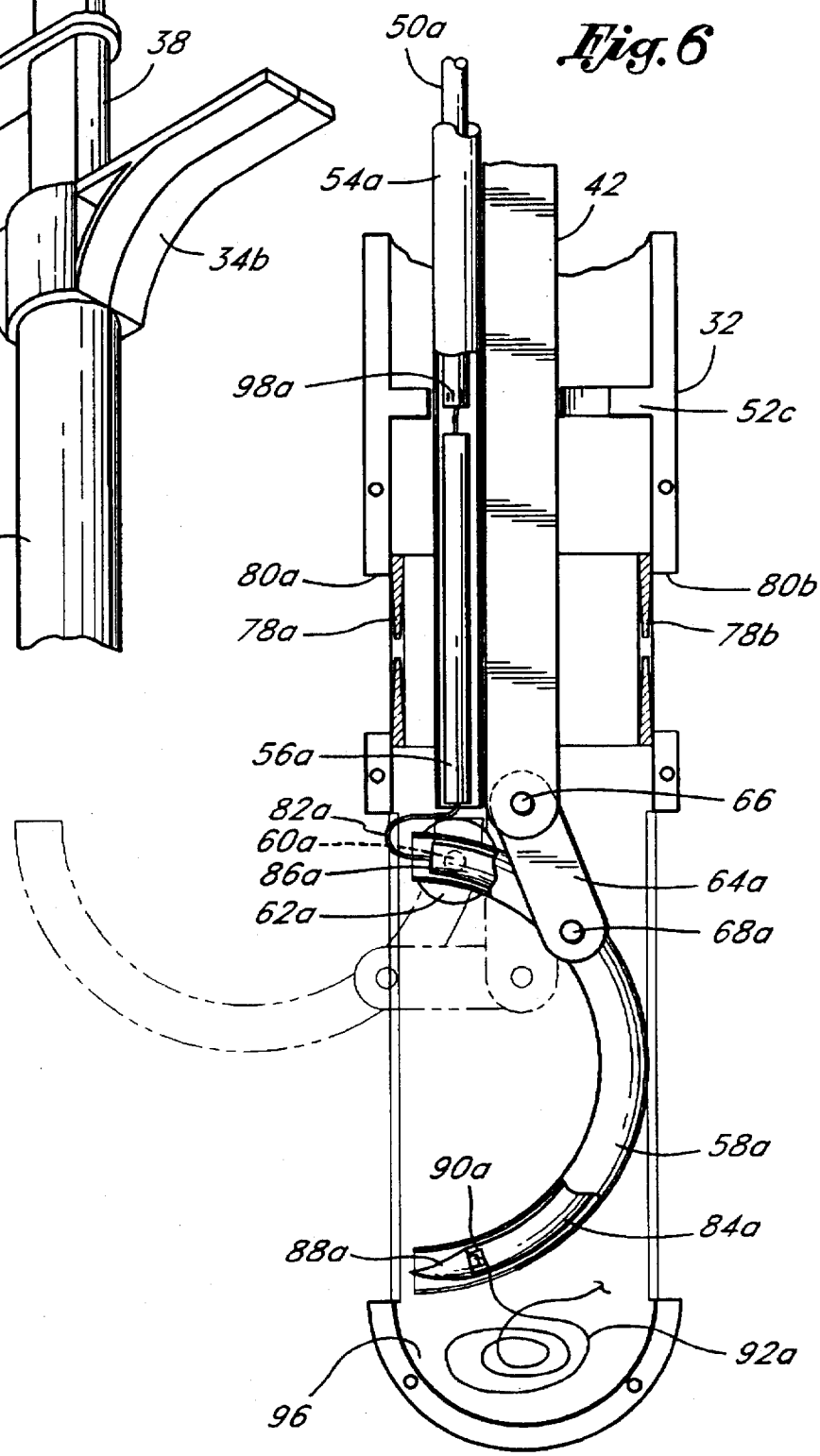

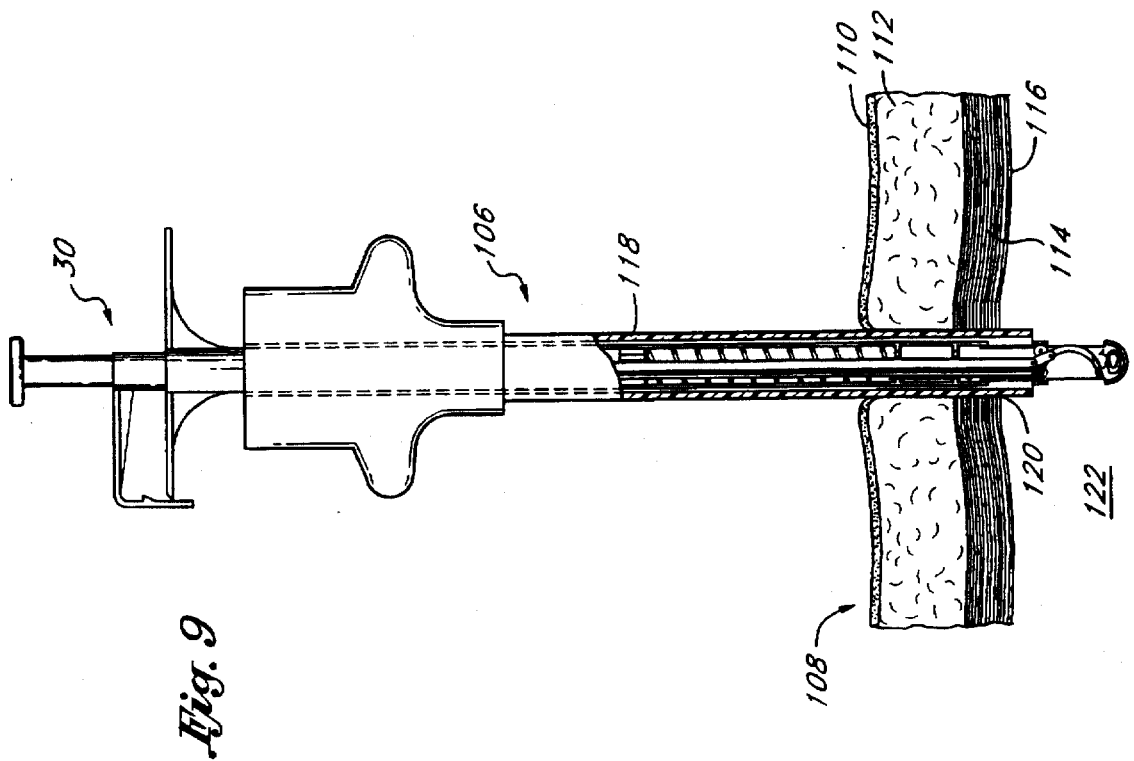
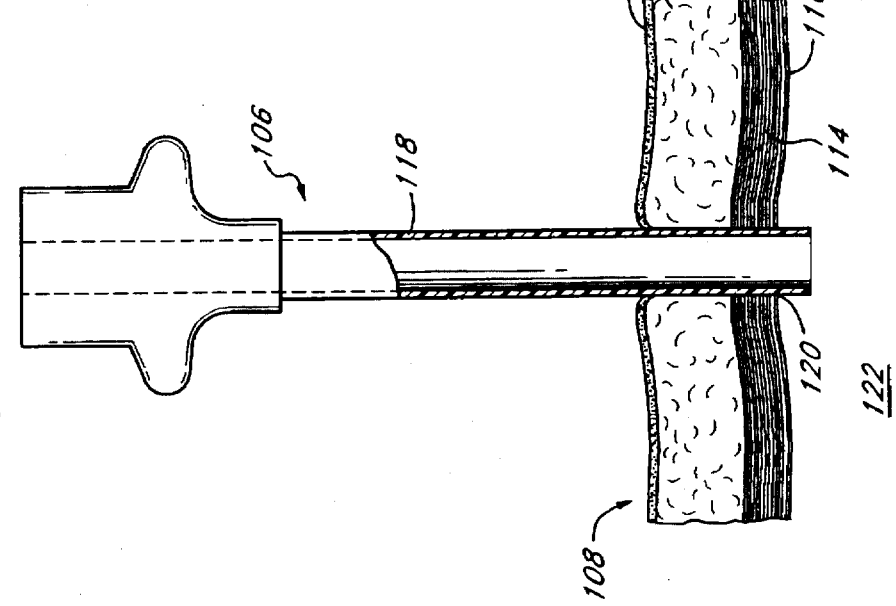

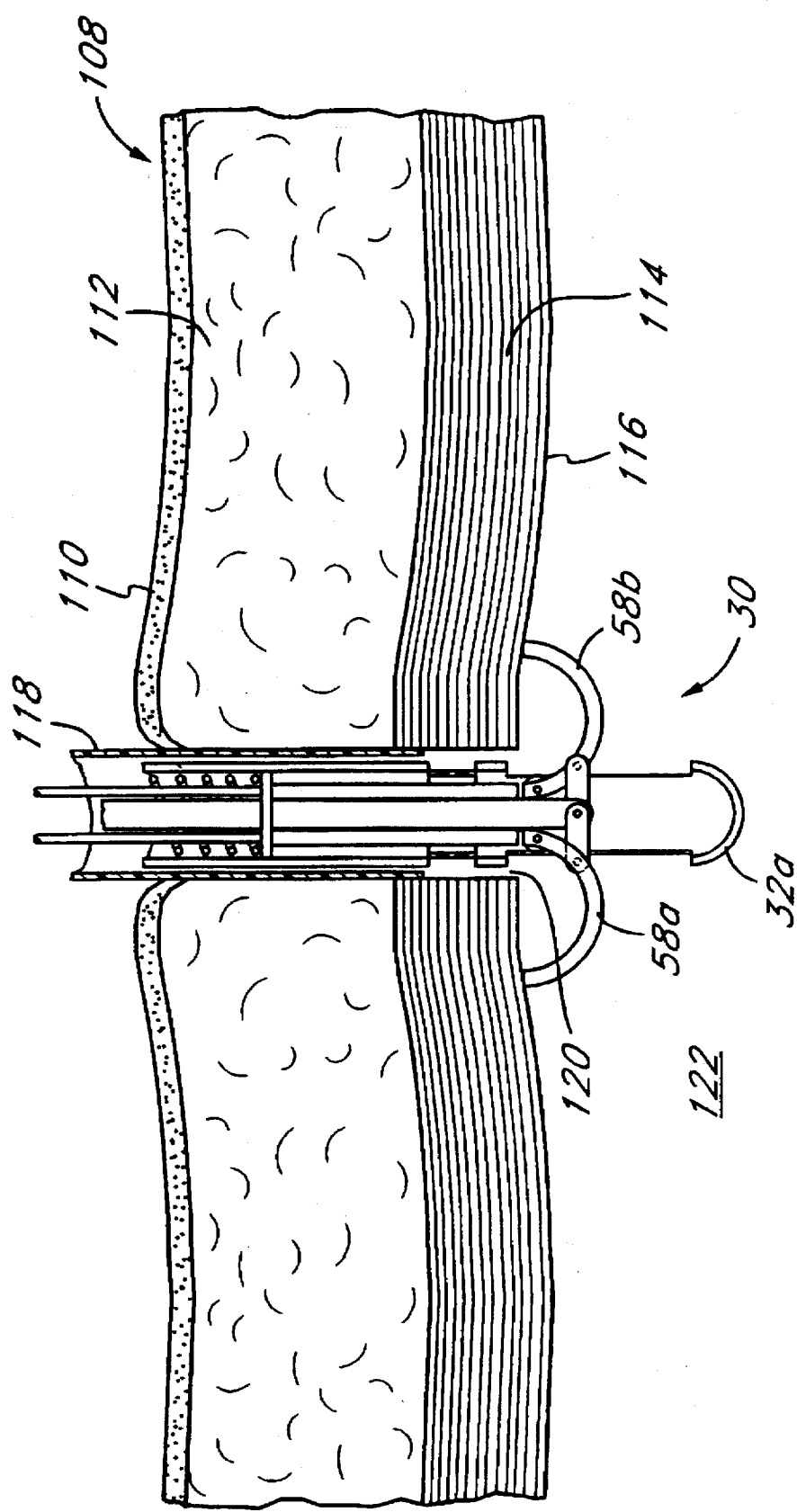

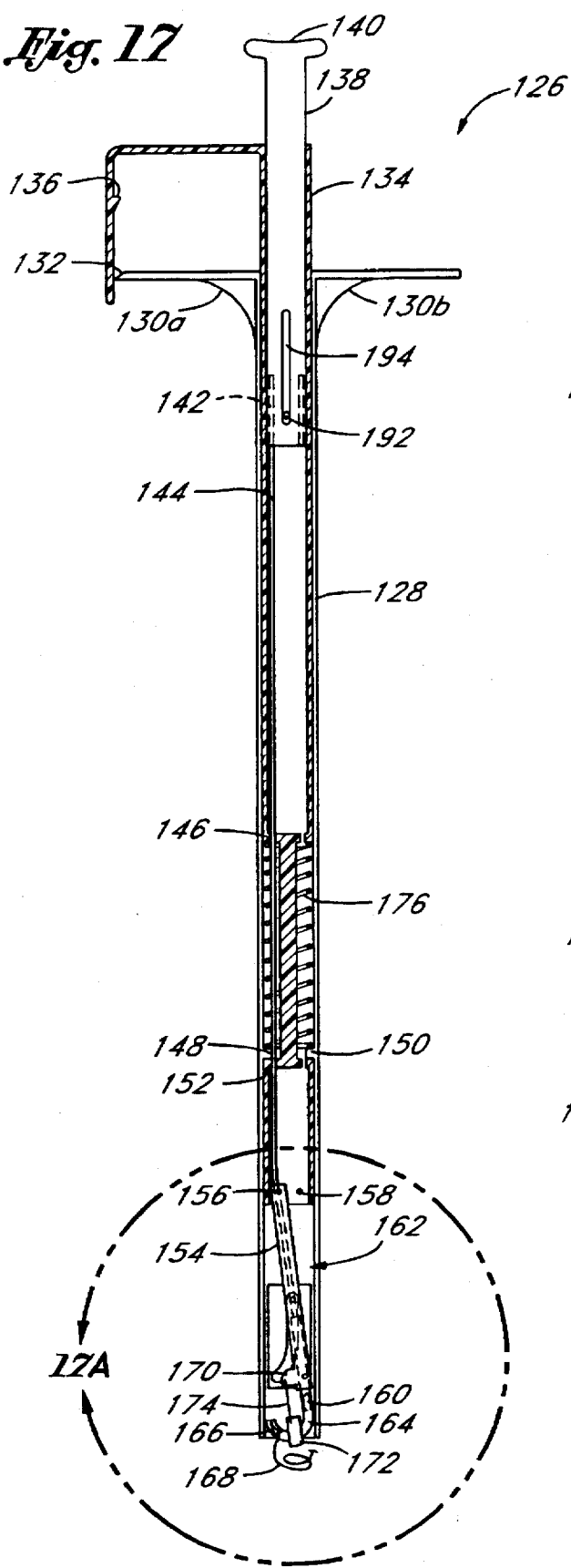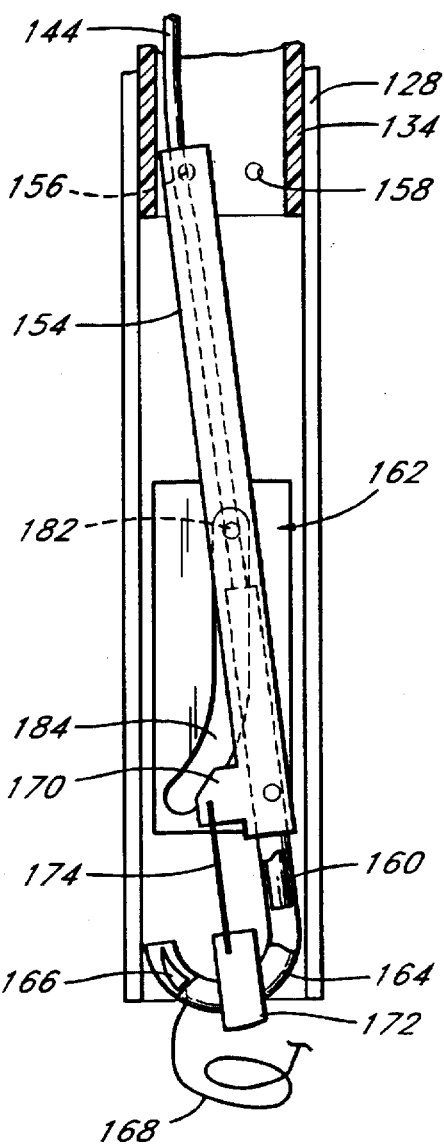

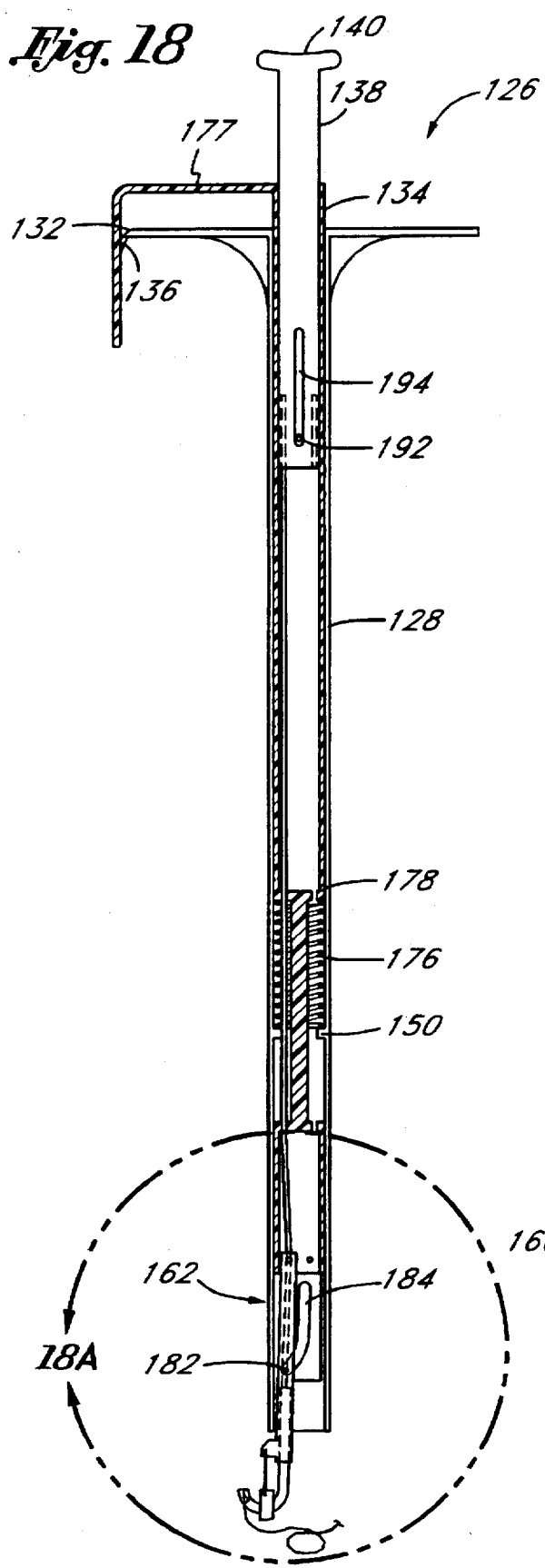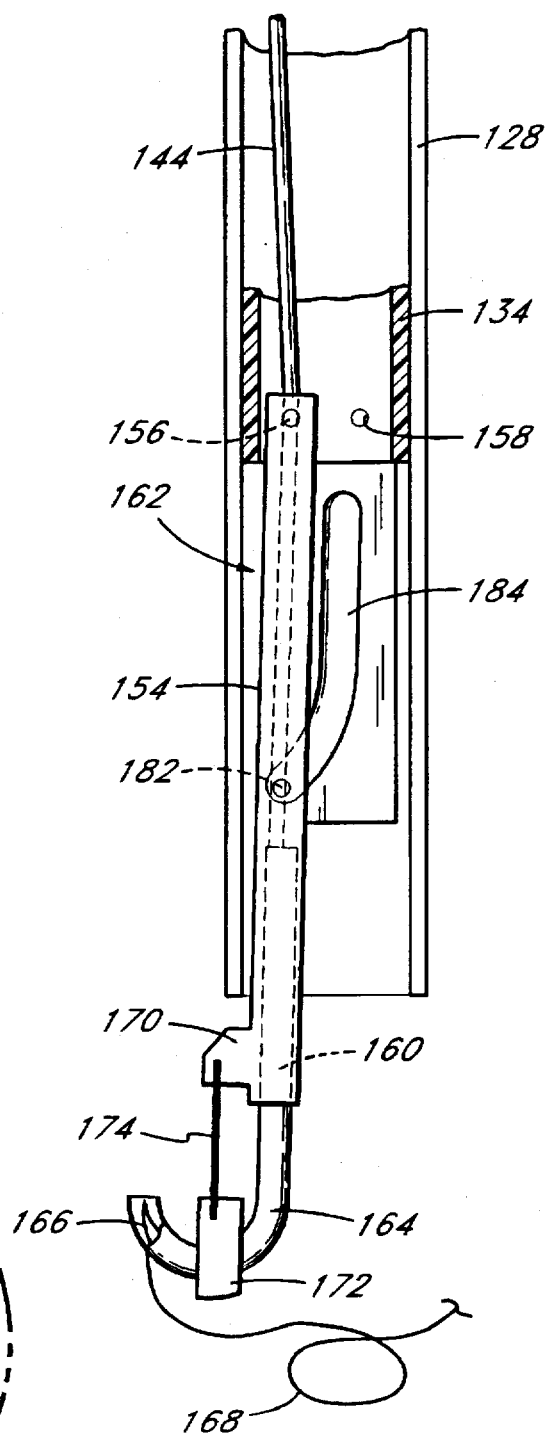

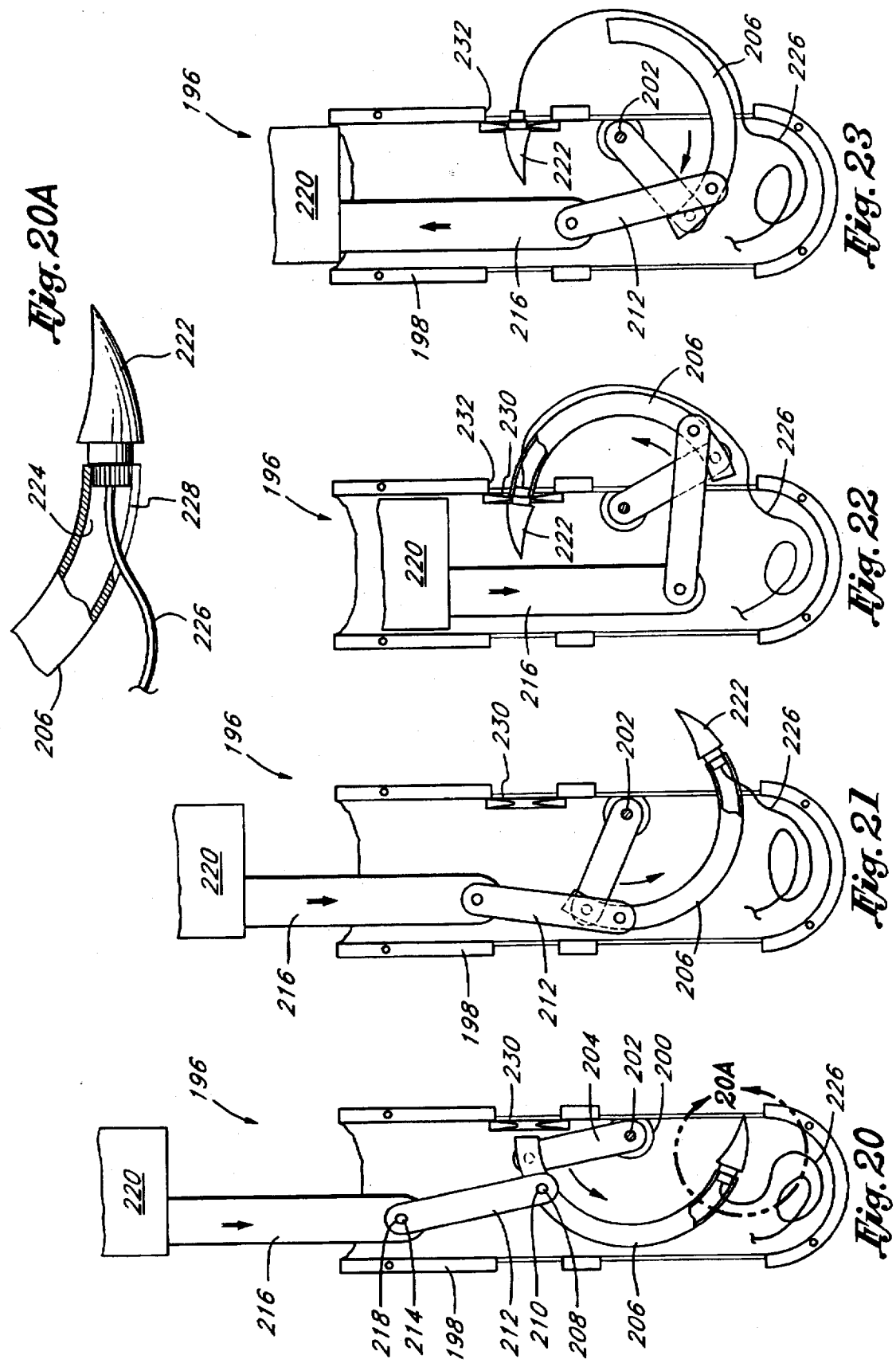

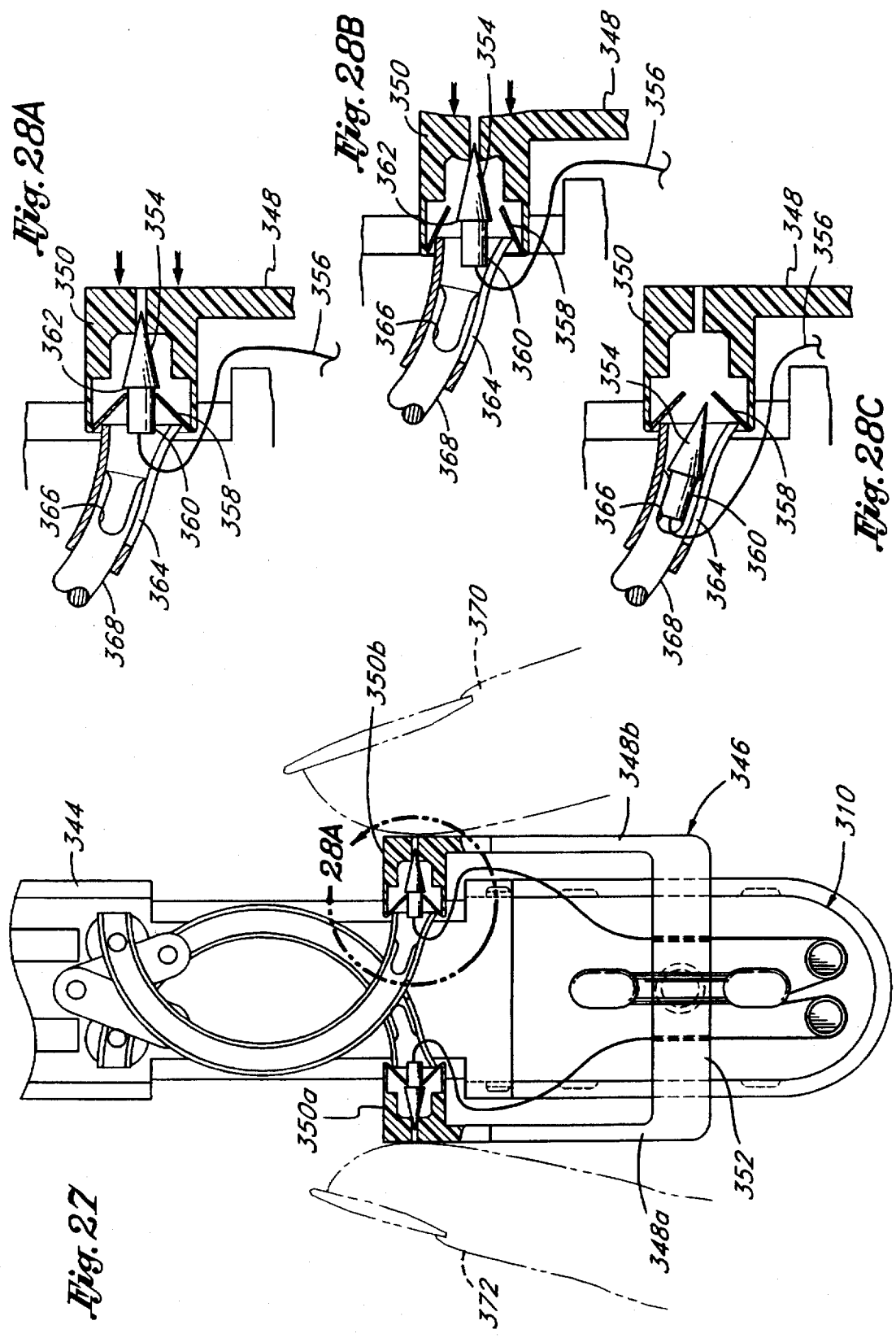

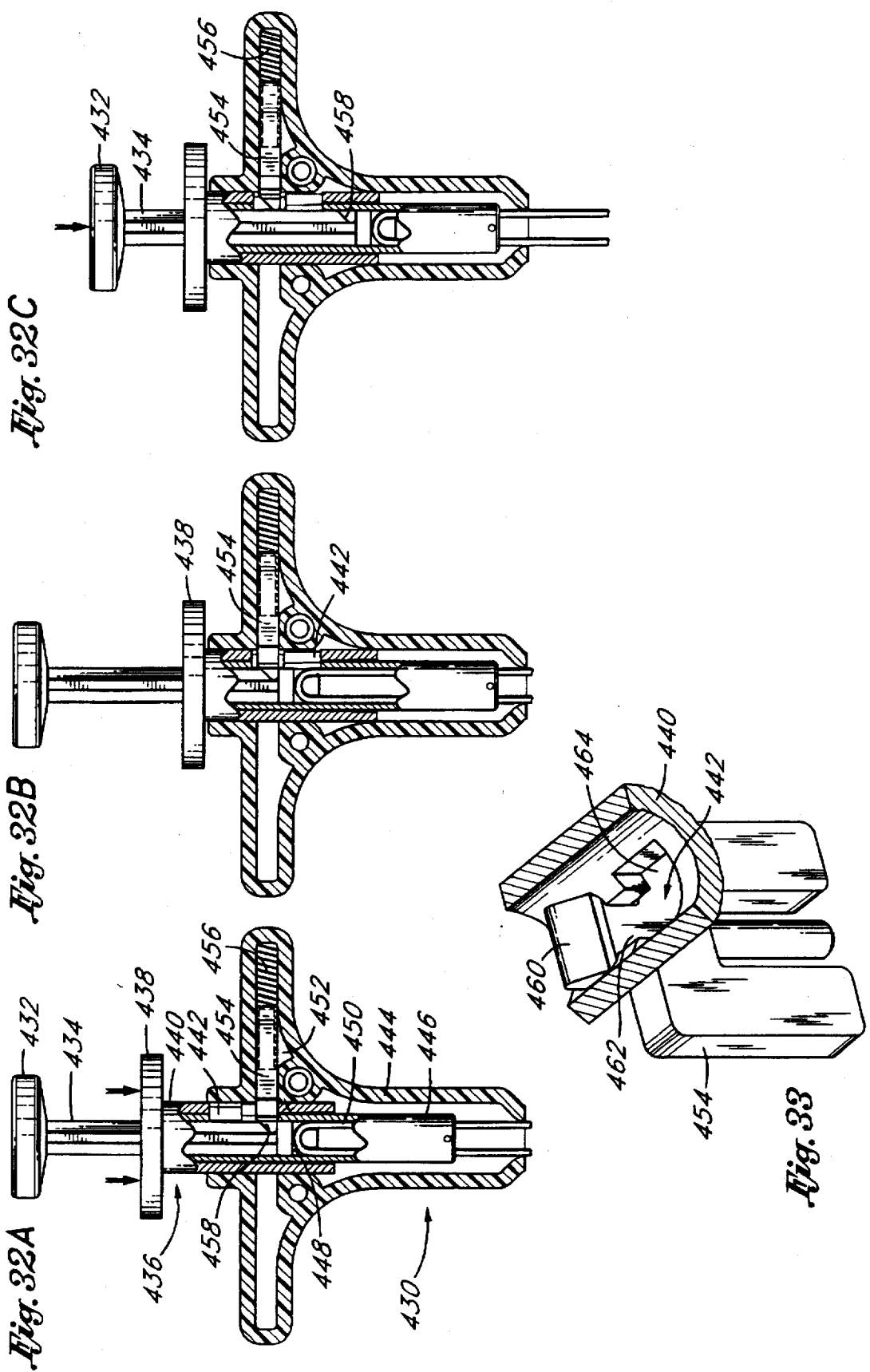

ENDOSCOPIC SUTURE SYSTEM

RELATED APPLICATION

This patent application is a Division of application Ser. No. 08/057,699; filed on May 4, 1993, by inventors Norman S. Gordon, Robert P. Cooper & Richard L. Quick and entitled "Endoscopic Suture System", now U.S. Pat. No. 5,458,609, which is a continuation-in-part of parent patent application Ser. No. 07/941,382, filed Sep. 4, 1992, by inventor Norman S. Gordon, and entitled "Endoscopic Suture System" now U.S. Pat. No. 5,364,408.

FIELD OF THE INVENTION

The invention relates to devices for approximation of tissue using a suture, and particularly to the tissue separated by means of an endosurgical trocar being inserted into a body cavity.

BACKGROUND OF THE INVENTION

Suturing of body tissues is a time consuming aspect of most surgical procedures. Many surgical procedures are currently being performed where it is necessary to make a large opening to expose the area of, for instance, the human body that requires surgical repair. There are instruments that are becoming increasingly available that allow the viewing of certain areas of the body through a small puncture wound without exposing the entire body cavity. These viewing instruments, called endoscopes, can be used in conjunction with specialized surgical instrumentation to detect, diagnose, and repair areas of the body that were previously only able to be repaired using traditional "open" surgery.

In the past, there have been many attempts to simplify the surgeons' task of driving a needle carrying suture through body tissues to approximate them. Many prior disclosures, such as described in Drake et al, U.S. Pat. No. 919,138 issued Apr. 20, 1909, employ a hollow needle driven through the tissue with the suture material passing through the hollow center lumen. The needle is withdrawn leaving the suture material in place, and the suture is tied, completing the approximation. A limitation of these type of devices is that they are particularly adapted for use in open surgical procedures where there is room for the surgeon to manipulate the instrument.

Others have attempted to devise suturing instruments that resemble traditional forceps, such as Bassett, U.S. Pat. No. 3,946,740 issued Mar. 30, 1976. These devices pinch tissue between opposing jaws and pass a needle from one jaw through the tissue to the other jaw, where grasping means pull the needle and suture material through the tissue. A limitation of these designs is that they also are adapted primarily for open surgery, in that they require exposure of the tissues to be sutured. This is a severe limitation in the case of endoscopic surgery.

The term "endosurgery" means endoscopic surgery or surgery performed using an endoscope. In conjunction with a video monitor, the endoscope becomes the surgeons' new eyes from which they operate. Operations using an endoscope are significantly less invasive when compared to traditional open surgery. Patients usually return home the next day or in some cases the same day of the endosurgical procedure. This is in contrast to standard open surgical procedures where a large incision divides the muscle layers and allows the surgeon to directly visualize the operative area. Patients may stay in the hospital for 5 to 6 days or longer following open surgery. In addition, after endosurgical procedures, patients return to work within a few days versus the traditional 3 to 4 weeks at home following open surgery.

Access to the operative site using endosurgical or minimally invasive techniques is accomplished by inserting small tubes called trocars into a body cavity. These tubes have a diameter of, for example, between 3 mm and 30 mm and a length of about 150 mm (6 inches). There have been attempts to devise instruments and methods for suturing within a body cavity through these trocar tubes. Such an instrument is disclosed by Mulhollan et al, U.S. Pat. No. 4,621,640 issued Nov. 11, 1986. Mulhollan describes an instrument that may be used to hold and drive a needle, but makes no provision for retrieval of the needle from the body cavity, nor the completion of the suture by tying. Another such instrument is described by Yoon, U.S. Pat. No. 4,935,027, issued Jun. 19, 1990. This instrument uses oppositional hollow needles or tracks pushed through the tissue and coapted to create a tract through which the suture material is pushed. It is not clear how these curved tracks would be adapted to both be able to pierce the tissue and be curved toward each other to form the hollow tract.

The invention herein described may be used for final closure of umbilical and secondary trocar puncture wounds in abdominal tissues including the fascia and other layers. The umbilical puncture is routinely a puncture site of 10 mm to 12 mm. Future procedures may require trocar puncture sites up to 18 mm and greater in size. Due to the large size of the puncture wound, it is important that the site be closed or approximated at the interior abdominal wall following removal of the large trocar cannula. An improper or non existent closure can lead to a herniation of the bowel and/or bowel obstruction. The present mode for closure is to reach down to the desired tissue layer with a pair of needle drivers holding a needle and suture material and secure a stitch. Many patients are obese and present considerable fat in this region. Because the abdominal wall may be several inches thick, it is extremely difficult, tedious and time consuming to approximate the fascial tissues with a suture. Often times, following removal of a large trocar, the puncture site needs to be enlarged to accomplish this, thus negating some of the advantages of endoscopic surgery previously discussed.

It is well known in the art that the use of particular suture materials for specific applications is desirable. In the case of closure of abdominal wall defects caused by operative wounds, trauma, or spontaneous separation, e.g. hernias, it is generally desirable to use an absorbable suture material. Such sutures may be made from synthetic materials such as polyglycolic acid, designed to be absorbed into the body by means of hydrolysis. As a result, these materials require specialized packaging and sterilization methods, known in the art as "bone dry" packaging. Such packaging processes are described by Glick in U.S. Pat. No. 4,135,622 issued Jan. 23, 1979 and assigned to American Cyanimid Corporation. Essentially, because of the sensitivity of these materials to degradation of tensile strength in the presence of moisture, they need to be sterilized and packaged in an environment that guarantees that they remain bone dry.

Due to these packaging constraints, it is desirable that the suture material along with the needles be packaged separately from the suture applicator. As a result, it is desirable to have a loading system that allows the user to quickly and easily place the needles and suture material into the applicator and prepare the applicator for use in the body. It will be clear to those skilled in the art that this loading system would be adaptable to include any of the available suture materials, such as silk, polyester, polypropylene, catgut and the like, even though these materials may not require the specialized packaging that the synthetic absorbable materials do.

None of the prior art devices are adaptable to effect the placement of a suture in the anterior abdominal wall. It is therefore an object of the present invention to provide a novel suturing device that overcomes the above set out disadvantages of prior known devices in a simple and economical manner.

It is a further object of the present invention to provide a suture device that will permit the approximation of the separated edges of a puncture wound without making a larger incision to expose the wound margins.

A further object of the present invention is to provide a suture device that will permit the surgeon to apply substantial force to the needle, permitting it to be driven through tough tissues, for example, the abdominal fascia.

It is a further object of the present invention to provide a suture device that can be used in conjunction with modern day endoscopic surgical techniques.

Yet another object of the invention is to provide a suture device that may be used to approximate the edges of an internal wound. Another object of the present invention to provide a suture device that permits the penetration of two needles having suture material extending there between into and through the sides of a wound and into catches thereby creating a suture loop through the wound that may be tied to approximate the tissues.

A further object of the present invention is to provide a loading system for suture material that allows the user to quickly and easily prepare the device for use.

Yet another object of the present invention is to provide a suture storage system which is compatible with current sterilization processes and incorporates the functionality of the above suture loading system.

SUMMARY OF THE INVENTION

The present invention is a new medical device that will allow the surgeon to quickly and easily place a suture in the interior wall of a body cavity to approximate the tissues separated as a result of a puncture wound made by the introduction of a surgical trocar into a body cavity during endoscopic surgery. The invention described herein may also be used to approximate the margins of an open wound in an internal organ, such as the uterus or the stomach, such as would be effected during the course of a resection for benign or malignant lesions. This may be done by adapting the device to allow for the needles to be actuated and driven independently.

The present invention includes needle holders that releasably hold a pair of needles that are in turn attached to each end of a single piece of suture material. Such needle holders are held within tubular guiding tracks housed within a hollow outer sleeve that may be introduced into a puncture wound. The needle holders and guiding tracks may be deployed outside the hollow sleeve to allow the needles to engage the tissue to be approximated. A plunger is coupled to rigid driving members that are in turn attached to flexible driving members adapted to follow the shape of the guiding tracks. The flexible driving members are suitably attached to the needle holders. The plunger is pushed, simultaneously driving the needle pair into opposite sides of the puncture wound and into catches also disposed within the hollow sleeve. The needle holders are retracted into the guiding tracks, and the tracks pulled back into the hollow sleeve trailing the suture material. The device may then be withdrawn, leaving a loop of suture material precisely placed in the selected tissue, for example, in the interior wall of the body cavity. The needles are removed from the ends of the suture, and the suture material is tied to complete the approximation of the tissue.

In one aspect, the present invention differs from the prior art in that it allows a suture to be placed in a retrograde fashion in the puncture wounds created during the introduction of trocars used for endoscopic surgery. These puncture wounds have margins perpendicular to the plane of tissue dissection, unlike the wounds that are addressed by prior art in which the tissues generally overlap. Presently all the existing instruments are designed to either approximate tissues to which direct visual and physical access may be gained during open surgery, or to approximate tissues that may be pinched between the jaws of a forceps like instrument. Wounds in body organs such as the uterus or the stomach which are created during the resection or removal of benign or malignant lesions may also have wound margins which require end to end approximation instead of overlapping. The present invention allows the surgeon to independently pass a needle through each side of the wound to allow the two sides to be drawn together, approximating the tissue.

The needle driver apparatus of the present invention may be constructed in a number of different ways. Several of the preferred ways are described herein. One embodiment uses needle guides which are semicircular in shape, holding either a semicircular needle, or a semicircular needle holder with a small needle tip. These guides are disposed across their diameter within a hollow tubular sleeve when in the retracted mode, and are rotated about one end to deploy them outside the bounds of the hollow sleeve for engaging the tissue to be sutured. The needles, or the needle holders, are driven through the tissue by axial movement of a rigid cylindrical member which contacts a flexible cylindrical member that follows the semicircular shape of the guide tracks. The needles are caught in catches placed within the hollow tubular sleeve that capture the needle by means of a leaf spring disposed to flex, preferably in one direction, and squeezing into grooves or recesses in the needles, thereby retaining the needles to the hollow tubular sleeve. The needle guides may be retracted, and the instrument removed from the wound, thus trailing the suture material. The needles are removed, the suture is tied, and the approximation is completed.

Another version of the device uses similar semicircular needle holders to the previous version, but the needle guides are eliminated. The needle holders are instead rotated about their axes such that the needles attached to the ends of the holders describe an arc that encompasses the tissue to be sutured.

Yet another embodiment of the device uses elongated guides with hooked ends, the ends describing semicircles, housed within a hollow tubular member. Into the hooked ends are placed needles with the suture material between. The needle guides are translated axially and then radially to dispose them outside the bounds of the hollow tubular member. The catches are attached directly to the needle guides, to allow for their precise placement relative to the needle path.

It is contemplated that the above embodiments may be modified to include needle paths other than circular, such as elliptical or straight, by modification of the needles, the needle holders and the needle guides. It is also possible to utilize a tool that would use only a single needle and guide it through both sides of the wound as opposed to the double needle configuration described above. It is also possible to adapt the above configurations to allow each of the needles to be actuated and driven independently by dividing the deployment controls and the needle drivers into separate left and right hand members.

In one embodiment, the present invention comprises a surgical suture device for applying a suture to approximate tissue surrounding a trocar puncture wound in a body cavity wall. The suture device comprises a first needle and a second needle attached to opposite ends of a length of suture material; a needle catch; a needle deployment mechanism for moving the first and second needles along first and second paths which terminate in the needle catch; and a cannular body member for inserting the first needle, the second needle, the suture material, the needle catch and the needle deployment mechanism into a body cavity through a puncture wound in a wall of the body cavity. The needle deployment mechanism transports the needles to regions outside of the cannular body member, into the body cavity wall and back into the cannular body member, thereby forming a loop of the suture which approximates tissue on opposing sides of the puncture wound when the cannular body member, along with the first needle, the second needle, the suture material, the needle catch and the needle deployment mechanism are extracted from the body cavity. This device may further include first and second needle guides for directing the first and second needles and/or first and second needle carriers for holding the first and second needles. For some applications, the needle carriers and needle guides have a substantially semi-circular shape. The device may further include a first flexible cylindrical member for pushing the first needle through the first needle guide.

Another embodiment of the invention is in the form of a suture device having a first needle having a suture attachment point; a second needle having a suture attachment point; a suture having a first end attached to the first needle suture attachment point and a second end attached to the second needle suture attachment point; a capture system for receiving and retaining the first and second needles; a needle deployment system for: a) moving the first needle along a first path which initially diverges away from the capture system and subsequently converges toward the capture system; and b) moving the second needle along a second path which initially diverges away from the capture system and subsequently converges toward the capture system; and a cannular body member having a chamber for containing the first and second needles; the suture; the needle deployment system; and the capture system.

In yet another embodiment, the invention describes a suture device comprising: a first needle and a second needle attached to opposite ends of a length of suture material contained within a tubular body member; and a needle deployment mechanism contained within the tubular body member for moving the first and second needles along first and second paths which traverse regions external to the body member and return to a catch mechanism on the body member. Additionally, first and second needle guides may be included which define the shape of the first and second paths traversed by the first and second needles.

An additional embodiment includes a suture application apparatus comprising: a needle attached to a suture; and a needle deployment mechanism which transports the needle along a path which first intercepts one side of a plane of reference, passes through the plane, reverses direction and then intercepts the opposite side of the plane.

The invention encompasses a method of approximating a trocar puncture wound in the wall of a body cavity. The method includes the following steps: 1) inserting a cannular body member having a chamber into the body cavity through the puncture wound, wherein the chamber contains a first needle and a second needle attached to opposite ends of a length of suture material, a needle catch device and a needle deployment mechanism; 2) extending the first needle into a first region of the wall of the body cavity adjacent the puncture wound and the second needle into a second region of the wall of the body cavity adjacent the puncture wound with the needle deployment mechanism; 3) capturing the first and second needles in the needle catch device; and 4) extracting the body member from the body cavity through the puncture wound, thereby forming a loop of the suture which is secured to opposing regions of the puncture wound.

The invention also incorporates a method of approximating a wound in a body organ within a body cavity. The method includes the following steps: 1) inserting a cannular body member having a chamber into the body cavity through a puncture wound, wherein the chamber contains a first needle and a second needle attached to opposite ends of a length of suture material, a needle catch device and a needle deployment mechanism; 2) extending the first needle into a first region of the wound of the body organ; 3) driving and capturing said first needle in the needle catch device; 4) extending the second needle into a second region of the wound of the body organ; 5) driving and capturing said second needle in the needle catch device; and 6) extracting the body member from the body cavity through the puncture wound, thereby forming a loop of the suture which is secured to opposing regions of the wound in the body organ.

In one embodiment, the present invention is for a suture device comprising: an elongate cannular body member which defines an internal chamber; a first actuator located near a proximal end of the cannular body member and extending into the internal chamber, the first actuator having a retracted position and a deployed position; and a first needle deployment mechanism comprising a needle carrier pivotally mounted within the internal chamber near a distal end of the elongate cannular body member, the first needle deployment mechanism connected to the first actuator and having a retracted configuration when the first actuator is in the retracted position wherein substantially all of the first needle deployment mechanism is contained within the internal chamber and a deployed configuration when the first actuator is in the deployed position wherein the first needle deployment mechanism transports the needle carrier outside of the internal chamber along a path having an initial direction away from the cannular body member as the first actuator begins to move from the retracted position toward the deployed position followed by a direction toward the cannular body member as the first actuator approaches the deployed position. This embodiment may further comprise a needle having a suture attachment point inserted in the needle carrier; a suture attached to the needle suture attachment point; and a needle capture system located on the cannular body member at a location which intercepts the portion of the needle carrier path which approaches toward the cannular body member. Alternatively, this embodiment may further comprise a second actuator and a second needle deployment mechanism which are deployable independently of the first actuator and the first needle deployment mechanism. A second alternative embodiment further comprises a second needle deployment mechanism which is deployable simultaneously with the first needle deployment mechanism by the first actuator, wherein the first and second needle deployment mechanisms are deployed on opposite sides of the cannular body member. In yet a third alternative embodiment, the suture device first actuator comprises a first sub-actuator and a second sub-actuator, each having a retracted position and a deployed position which is independent of the other, wherein the first needle deployment mechanism transports the needle carrier outside of the internal chamber along the path having an initial direction away from the cannular body member as the first sub-actuator moves from the retracted position toward the deployed position followed by the direction toward the cannular body member as the second sub-actuator moves from the retracted position toward the deployed position.

The invention also encompasses a suturing apparatus for securing a suture at a location within a confined space, wherein the apparatus comprises: a cartridge, wherein the cartridge further comprises: a cartridge body member having an attachment point; and a first needle and a second needle attached to opposite ends of a length of suture material mounted on the cartridge body member; and an applicator tool, wherein the applicator tool further comprises: an applicator tool body member which defines an internal cavity, the applicator tool body member including an attachment point which joins with the cartridge body member attachment point; and a needle deployment mechanism contained within the applicator tool body member internal cavity, the needle deployment mechanism holding the first and second needles and having a first position wherein the first and second needles are contained within the body member internal cavity and a second position wherein the first and second needles are located outside of the body member internal cavity. In this embodiment, the needle deployment mechanism may further comprise first and second needle carriers for holding the first and second needles. Additionally, the first and second needle carriers may have a substantially semi-circular shape.

The invention also includes a surgical needle comprising an elongate body section with a substantially uniform cross sectional area having a distal end, a pointed proximate end and a shoulder located intermediate the distal end and the pointed proximate end, the shoulder defined by an abrupt change in the cross sectional area of the body section, the transition between the body section and the shoulder defining a plane which is substantially perpendicular to a longitudinal axis of the elongate body section. In this embodiment, the elongate body section may take on a variety of cross section shapes including but not limited to conical, rectangular, or triangular. The surgical needle of this embodiment may further comprise a means for attaching a suture to the body section distal end. Additionally, this means for attaching a suture to the body section distal end may further comprise an eye formed in the body section.

Yet another embodiment of the invention includes a suture cartridge for use with a suture applicator, the suture cartridge comprising: a needle; a suture attached to the needle; and a support which holds the needle and suture in a predetermined configuration with respect to the support, the support further including a means for attaching the suture cartridge to the suture applicator. Additionally, the suture cartridge may further comprise an alignment element which aligns the cartridge with the suture applicator in a predetermined configuration. In another variation, the suture cartridge may further comprise a needle loader for loading the needle into the suture applicator, the loader comprising a body member having a needle pocket and a needle retainer which holds the needle in the pocket, the loader body member further including an alignment feature which positions the needle in a predetermined configuration with respect to the suture applicator.

The invention further includes a needle loading device for loading a surgical needle into a suturing tool, the loading device comprising a body member having a needle pocket and a needle retainer which holds the needle in the pocket, the loading device body member further including an alignment feature which positions the needle in a predetermined configuration with respect to the suturing tool.

Another embodiment of the invention is a suturing apparatus comprising: a suture cartridge comprising: a needle; a suture attached to the needle; and a support which holds the needle and suture in a predetermined configuration with respect to the support, the support further including a tool attach fixture; and an applicator tool, wherein the applicator tool further comprises: an applicator body member which defines an internal cavity, the applicator body member including an attachment fixture which, in combination with the cartridge support tool attach fixture, mounts the suture cartridge to the applicator tool; and a needle deployment mechanism contained within the applicator body member internal cavity, the mechanism having a first position wherein the needle is contained within the body member internal cavity and a second position wherein the needle is located outside of the body member internal cavity. This embodiment may further include a needle loader comprising a body member having a needle pocket and a needle retainer which holds the needle in the pocket, the needle loader body member further including an alignment feature which positions the needle in a predetermined configuration with respect to the needle deployment mechanism.

Another embodiment of a suturing apparatus is characterized by a needle comprising a point which is connected to a shoulder by means of a tapered section wherein the connection of the tapered section to the shoulder defines a first cross sectional transverse dimension of the shoulder, the shoulder further connected to a distal portion of the needle immediately adjacent the connection of the tapered section with the shoulder, wherein the connection of the distal section to the shoulder defines a second cross sectional transverse dimension of the shoulder which is smaller than the first cross sectional transverse dimension of the shoulder thereby forming a shoulder ledge; a suture attached to the distal portion of the needle; and a needle catch comprising a flexible aperture having a first relaxed dimension which is smaller than the first cross sectional transverse dimension of the shoulder but allows insertion of the needle into the aperture along an insertion direction by expansion of the flexible aperture first relaxed dimension to a stretched dimension which is substantially equal to the first cross sectional transverse dimension of the shoulder by the passage of the tapered section, the aperture returning to a second relaxed dimension, also smaller than the first cross sectional transverse dimension of the shoulder, the shoulder ledge thereby preventing removal of the needle from the catch in a direction which is the reverse of the insertion direction. In this embodiment, the needle catch may further comprise a removal aperture, contiguous with the flexible aperture, the removal aperture having a dimension which is larger than the first cross sectional transverse dimension of the shoulder, thereby allowing the needle to be removed from the needle catch when the needle is moved from the flexible aperture to the removal aperture.

The invention also describes a passive needle catch for receiving and retaining a shouldered surgical needle, the catch comprising a flexible aperture which expands to allow passage of the needle shoulder into the aperture and contracts after the needle shoulder has passed through the aperture. This passive needle catch may further comprise a removal aperture, contiguous with the flexible aperture, the removal aperture having a dimension which is larger than the needle shoulder, thereby allowing the needle to be removed from the needle catch when the needle is moved from the flexible aperture to the removal aperture.

The invention further includes a passive needle catch for a shouldered surgical needle, the catch comprising an aperture having a first region which has a dimension which is at least as large as the needle shoulder thereby allowing passage of the shoulder through the aperture, the catch further having a second region which has a dimension which is smaller than the needle shoulder, thereby preventing passage of the shoulder through the aperture.

These and other characteristics of the present invention will become apparent through reference to the following detailed description of the preferred embodiments and accompanying drawings.

BRIEF DESCRIPTION OF THE DRAWINGS

These and other objects and advantages of the subject invention will become more fully apparent from a reading of the following description in conjunction with the drawings wherein:

FIGS. 1A through 1H illustrate the general structure and operation of the present invention.

FIG. 2 is a cross sectional plan view showing a single needle guide inside a cannula.

FIG. 3 is a cross sectional plan view showing the needle guide in the deployed position.

FIG. 4A is a detailed perspective view showing that there are two needle guides.

FIG. 4B is a detailed perspective view showing only one of the needle guides in the deployed position.

FIG. 5 is a detailed perspective view of the top section of the device showing the deployment catch mechanism.

FIG. 6 is a detailed plan view of a swinging needle guide positioned in the cannula and a phantom view showing the needle guide in the deployed position.

FIG. 8 is a cross sectional side view of the abdomen with a trocar inserted, showing the wound in the abdominal wall.

FIG. 9 is a cross sectional side view of the present invention in place in the abdomen.

FIG. 10 is a detail cross sectional side view of the present invention in place in the abdomen with the needle guides deployed.

FIG. 17 is a detail plan view of an elongate needle guide design with the guides contained within a cannula.

FIG. 17A is an enlargement of the end of the embodiment shown in FIG. 17.

FIG. 18 is a detail plan view of the elongate needle guide design with the guides in the deployed position.

FIG. 18A is an enlargement of the end of the embodiment shown in FIG. 18.

FIG. 20 is a detail plan view of the semicircular needle holder without a needle guide with the holder positioned within the cannula.

FIG. 20A is a detail sectional view of the needle holder and needle assembly.

FIG. 21 is a detail plan view of the semicircular needle holder being deployed.

FIG. 22 is a detail plan view of the semicircular needle holder pushing the needle into the catch.

FIG. 23 is a detail plan view of the semicircular needle holder with the holder being retracted.

FIG. 27 is a detail cross sectional plan view of an alternate embodiment of a suture loading system.

FIGS. 28A through 28C are detail cross sectional plan views which illustrate the insertion of the needle into the needle carrier.

FIGS. 32A through 32C show sectional detail plan views of a suture device interlock assembly in its initial, first stage of deployment and second stage of deployment configurations, respectively.

FIG. 33 shows a detail perspective view of a lockout pawl in the interlock assembly.

DETAILED DESCRIPTION OF THE PREFERRED EMBODIMENTS

Although the principles of the present invention are applicable to any device suitable for use in surgical procedures, whether performed on humans or animals, particular utility is effected in human abdominal surgery performed using endoscopic techniques for closure of the wounds created during the introduction of trocars into the abdominal cavity, and particularly the puncture wounds created thereof, as well as closure or approximation of the wounds created either during the resection of benign or malignant lesions, or during the performance of other therapeutic procedures on an organ or organs within a body cavity.

Figure 1C:
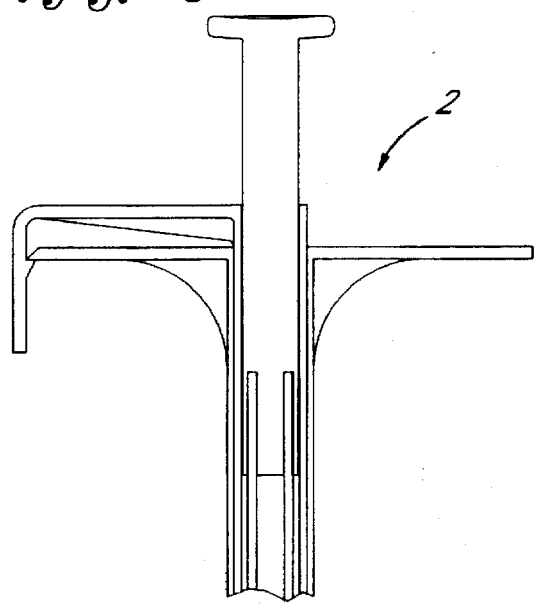
Figure 1D:
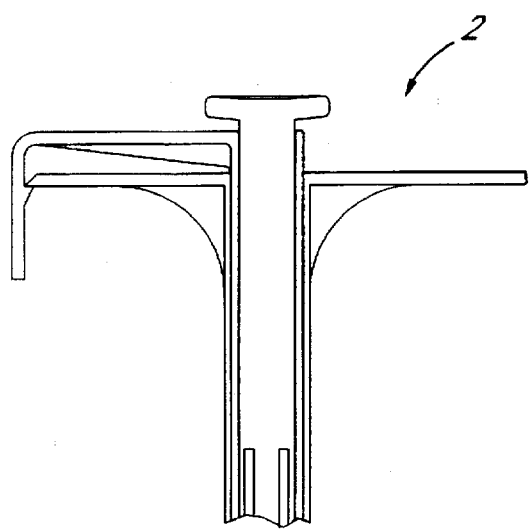
Figure 1E:
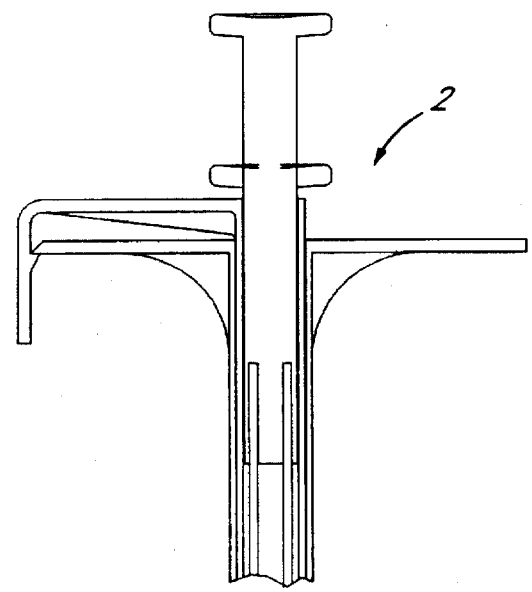
Figure 1F:
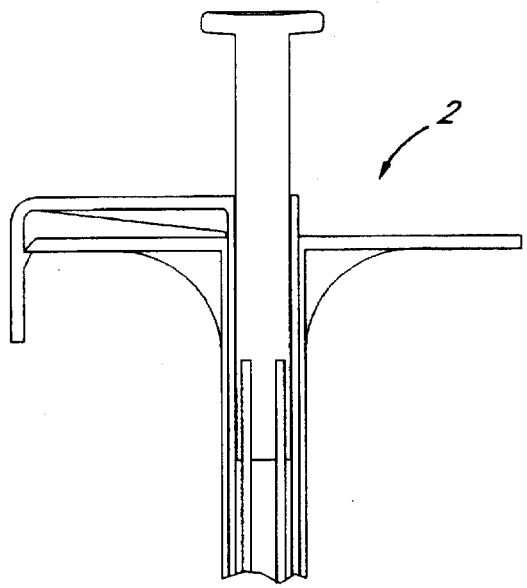

FIGS. 1A through 1H illustrate the general structure and operation of the present invention. FIGS. 1A and 1B show a device 2, according to the present invention, which incorporates a length of standard suture material 4 with a needle 6 on each end. The needles 6 are held by a needle carrier 8 (FIG. 1D) and loaded into two guiding tracks 10. The guiding tracks 10, containing the needle carriers 8 and needles 6, are deployable outside a housing 12 of the device 2 to allow the suture material 4 to be placed outside the limits of a puncture wound 14 (FIGS. 1B and 1C). After deployment of the guiding tracks 10 (with the needle carriers 8 and needles 6 contained within) the needle carriers 8 and needles 6 are driven out of the guiding tracks 10 and into tissue surrounding the puncture wound 14 (FIGS. 1C and 1D). The needles 6 are driven into a catch mechanism 16 (FIG. 1D). The needle carriers 8 are retracted back into the guiding tracks 10 (FIG. 1E). The guiding tracks 10 (now containing only the needle carriers 8 without the needles 6) and the catch mechanism 16 with the captured needles 6, are retracted as shown in FIGS. 1F, 1G and 1H. With a loop of suture 4 having thus been placed in the tissue surrounding the puncture wound 14, the suture device 2 is removed from the wound 14, thereby pulling the ends of the suture 4 with it (FIG. 1H). Closure of the puncture wound 14 is accomplished by cutting the suture 4 to remove the needles 6, tying a knot in the suture 4, and pushing it into the wound 14. Superficial closure is then performed by normal means according to the surgeon's preference.

Detailed drawings of an illustrative embodiment of the invention are shown in FIGS. 2, 3, 4A, 4B, 5, 6 and 7 wherein a suture application device 30 includes an outer housing 32, with finger grips 34a and 34b, and a deployment catch 36. The outer housing 32 is preferably made of injection molded plastic such as polycarbonate, as are many other of the components described herein. A deployment sleeve 38, slidably disposed within the outer housing 32, has a retention catch 40 and is attached to a pushrod 42, constructed for example, of stainless steel. A driver shaft 44 includes a button 46 and has a hole 48a, into which is bonded an elongate rigid shaft 50a. The rigid shaft 50a, which may be made of music wire, passes through outer housing ribs 52a, 52b and 52c, and as best shown in FIG. 4A, terminates slidably disposed within a hollow cylinder 54a. The hollow cylinders 54a and 54b, preferably made from stainless hypodermic tubing, are held in recesses in the outer housing ribs 52b and 52c. An elongate flexible tubular member 56a, that may be made of polypropylene or other suitable material, is also slidably disposed within the hollow cylinder 54a. As shown in FIG. 6, needle guide 58a may also be constructed from stainless hypodermic tubing, and has pivot pins 60a and 60b pivotally disposed within outer housing bosses 62a and 62b. A driving link 64a is attached by a link pin 66 to the pushrod 42 and to the needle guide. 58a by a pivot pin 68a, with the entire mechanism preferably made of stainless steel so as to maximize the biocompatibility as well as the strength of the actuating members. It may be appreciated from FIG. 4A that, as described, there are two needle guides 58a and 58b oppositionally disposed within the outer housing 32.

Referring again to FIGS. 2 and 3, a driver retainer 70 is slidably disposed within the outer housing 32, and is fixably attached to rigid shafts 50a and 50b, with a hole 72 to allow the pushrod 42 to pass slidably therethrough. A driver spring 74, preferably wound from stainless steel wire is compressed between the driver retainer 70 and the outer housing rib 52b. A deployment spring 76, also made of stainless steel wire is compressed between an end 77 of the deployment sleeve 38 and outer housing rib 52a. A needle catch 78a is housed within a recess 80a in the outer housing 32.

Referring now to FIG. 6, a retraction line 82a that is preferably made of kevlar, is slidably threaded through the flexible tubular member 56a and is attached to a needle carrier 84a by means of a crimp 86a or other means that would bind the retraction line 82a to the needle carrier 84a. The distal end of the retraction line 82a is attached to the rigid shaft 50a by means of another crimp 98a or other means. The needle carrier 84a is slidably disposed within the needle guide 58a, and holds a needle 88a, typically constructed of surgical grade stainless steel in a recess 90a, such needle having a suture 92a attached thereto. The suture material is preferably polyglycolic acid, but may be made of polypropylene, nylon, silk, catgut, or any other materials known in the art selected for their biocompatibility and tensile strength to be used in the body for the approximation of tissue. The suture 92a exits the needle guide 58a by means of a groove 94a (groove 94a is hidden from view in FIGS. 4A and 4B, however, groove 94b in the opposing needle guide 58b is visible), and is stored in a recess 96 in outer housing 32.

Figure 7:
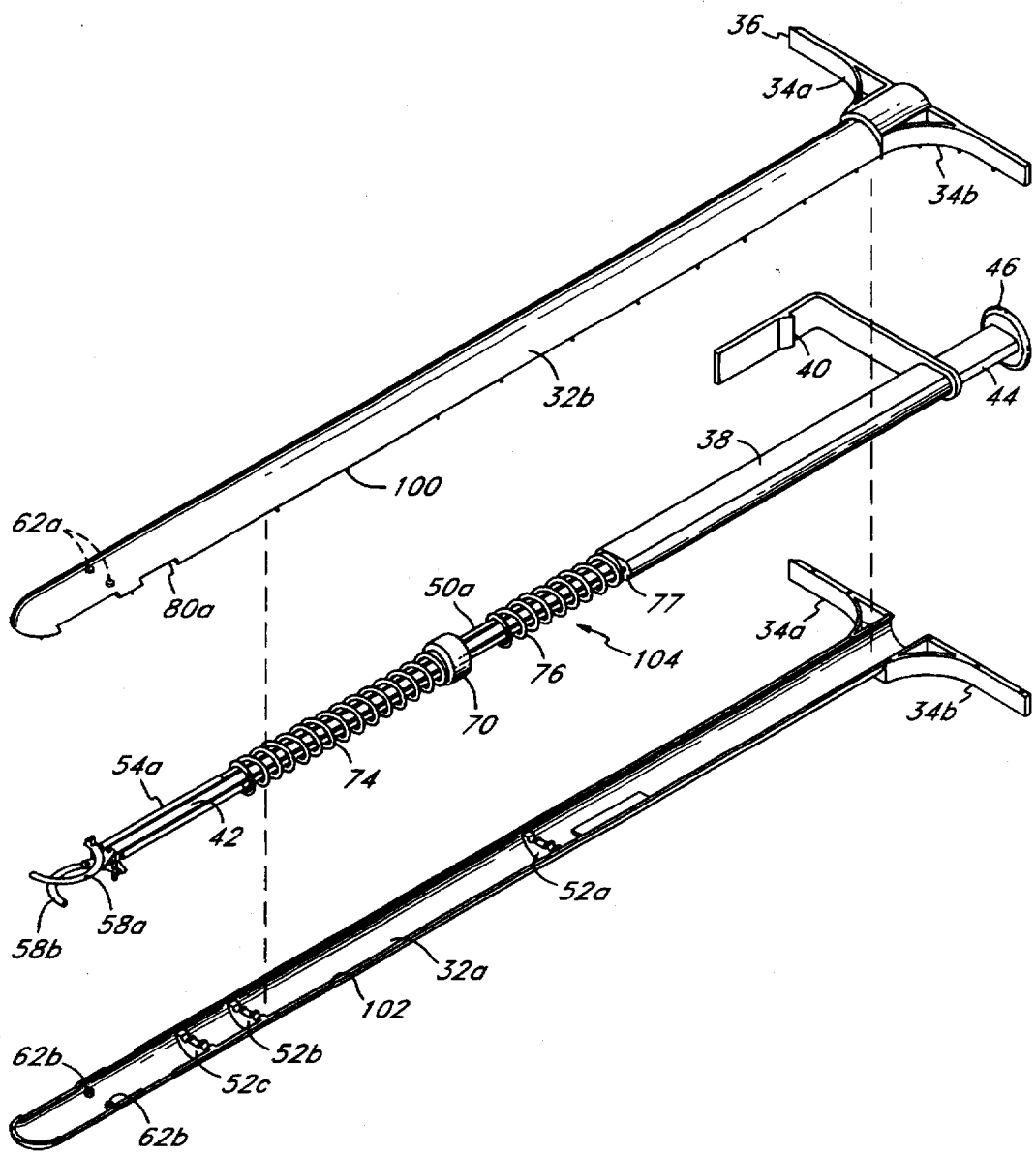
FIG. 7 is an exploded perspective view of the major components of the present invention.

Referring to FIG. 7, it may be seen that outer housing 32 may comprise two halves, 32a and 32b which are joined by pins 100 and holes 102. The pins 100 and holes 120 are preferably molded into the outer housing halves 32a and 32b to encompass an inner assembly 104.

Use and operation of this embodiment of the invention will be described beginning with reference to FIG. 8 which shows a trocar assembly 106 inserted into the abdominal wall 108, which includes a layer of skin 110, a fat layer 112, a muscle layer 114 and a fascial layer 116. The trocar assembly 106 includes a hollow tube 118 that is inserted through the abdominal wall 108 and into an abdominal cavity 122 using techniques well known to those skilled in the art, creating a puncture wound 120. As shown in FIG. 9, the suture application device 30 of the present invention is inserted through the hollow tube 118 into the trocar assembly 106 until it passes into the abdominal cavity 122. Referring to FIG. 3, arm 124 of deployment sleeve 38 is pushed so that the sleeve slides within the outer housing 32, compressing spring 76, and in turn sliding pushrod 42. As can be seen in FIGS. 4A and 4B, when the pushrod 42 slides relative to the outer housing 32, driving links 64, which are pivotally attached to both pushrod 42 and needle guides 58, force the needle guides 58 to pivot about the pins 60 that are retained in outer housing bosses 62. The ultimate deployed position of one of the needle guides 58a is shown in perspective view in FIG. 4B and in cross sectional plan view in place in the body in FIG. 10. Referring to FIG. 10, it can be seen that the suture device 30 is in place through the hollow tube 118 and in the abdominal cavity 122, with needle guides 58 deployed and engaging the fascial layer 116 and the muscle layer 114.

Figure 12:
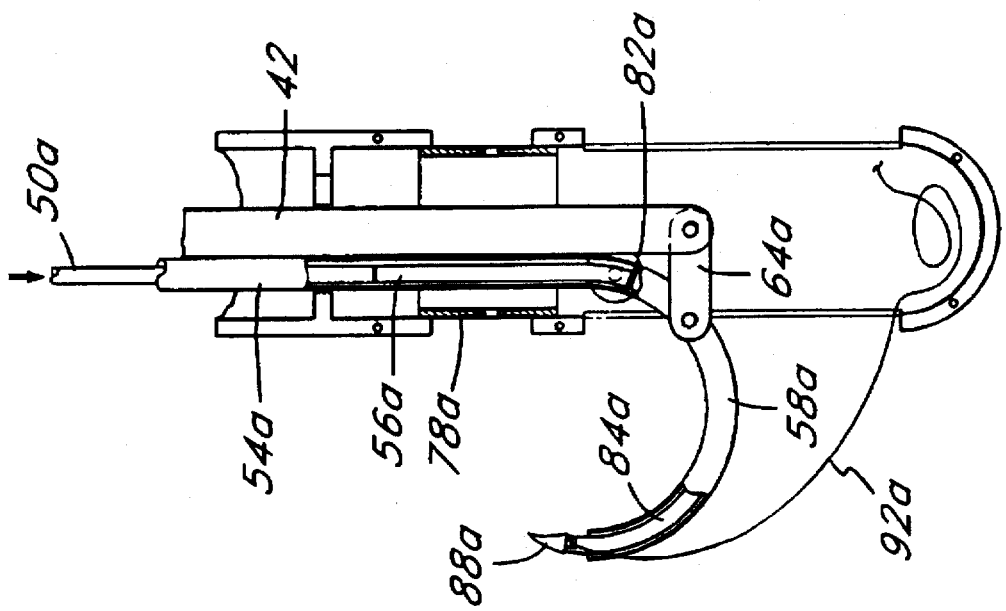
FIG. 12 is a detail plan view similar to view 6 showing a flexible member being pushed into the guide.
Figure 11:
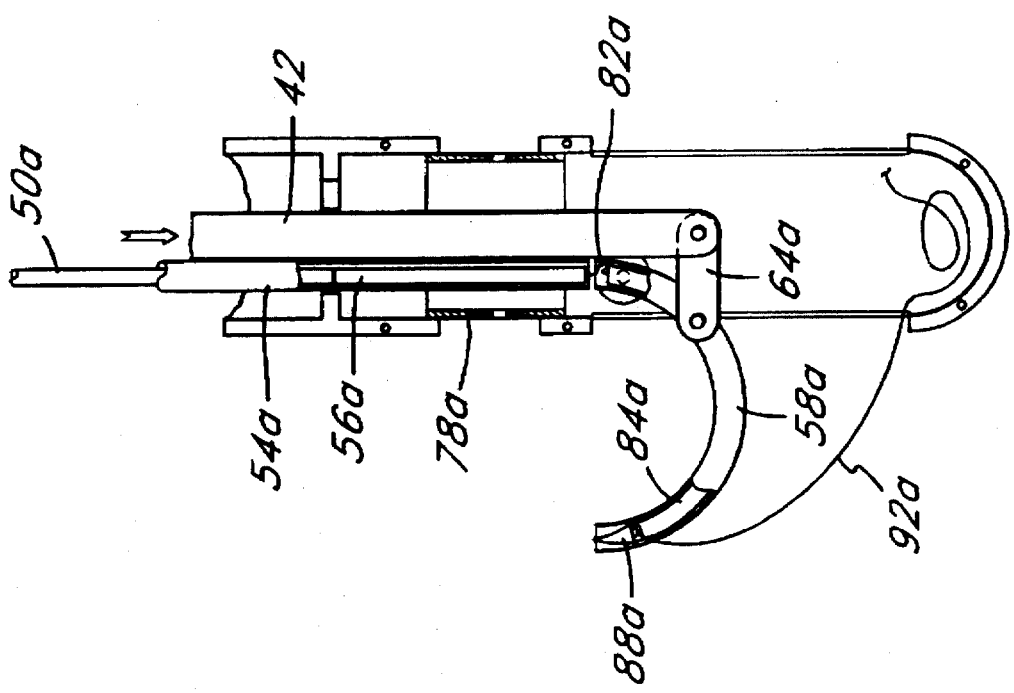
FIG. 11 is a detail plan view similar to view 6 showing a needle in a guide with the guide deployed.
Figure 13:
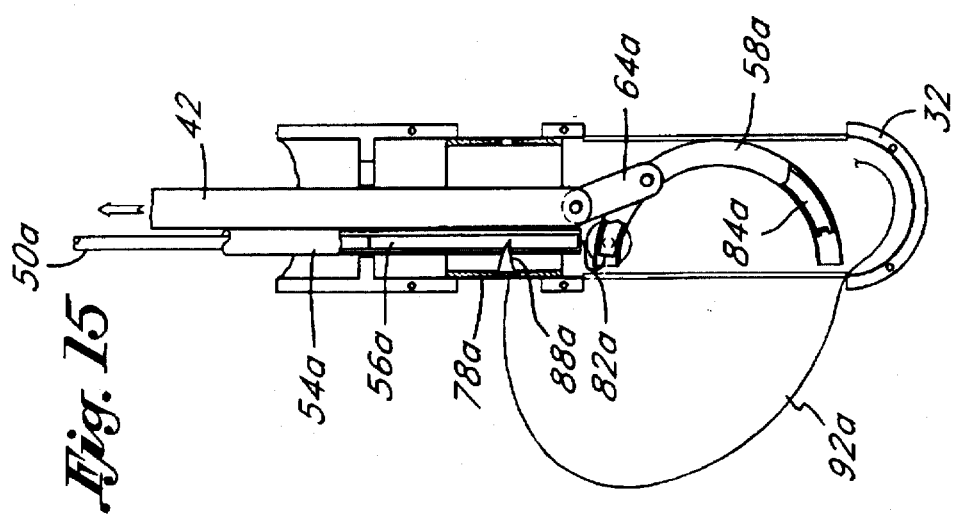
FIG. 13 is a detail plan view similar to view 6 showing a needle being pushed into a catch.
Figure 14:
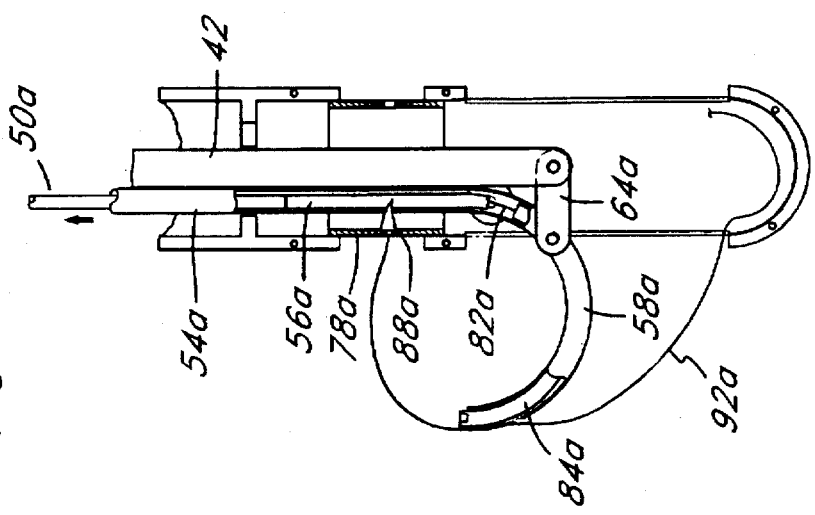
FIG. 14 is a detail plan view similar to view 6 showing the needle carrier being retracted, the needle secured in the catch and trailing a suture.
Figure 15:
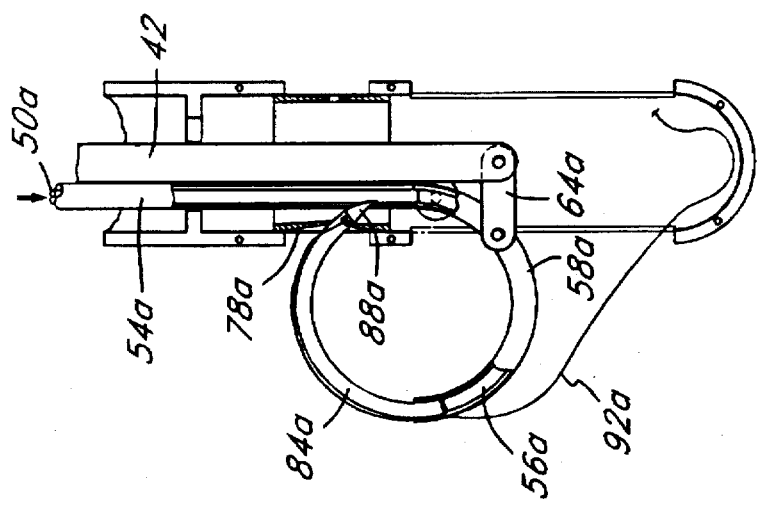
FIG. 15 is a detail plan view similar to view 6 showing the needle guide retracted back into the housing.
Figure 16:
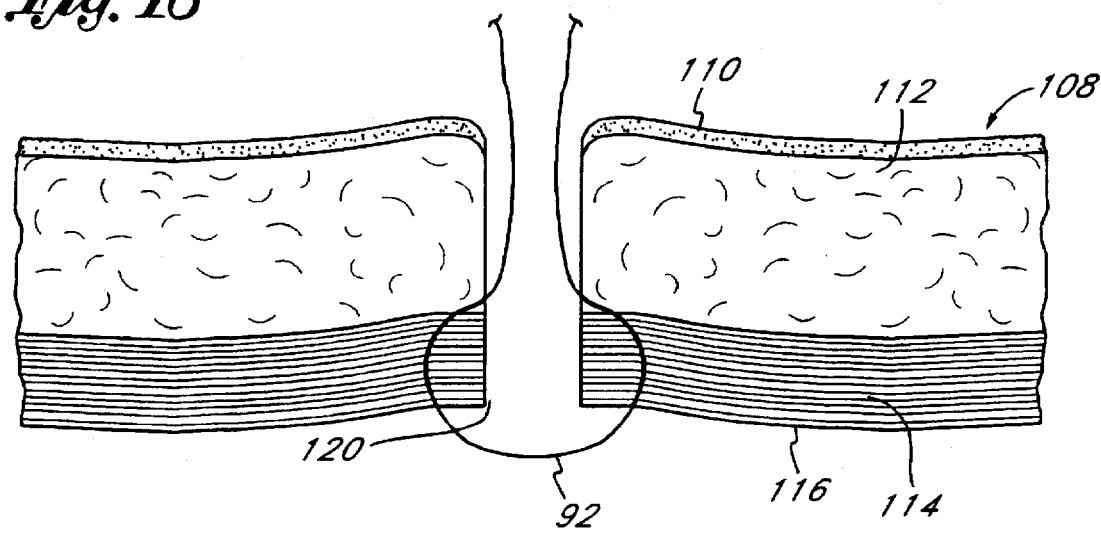
FIG. 16 is a detail plan view similar to view 6 showing the suture left in place in the wound before tying.

Operation of the needle driver portion of this embodiment will be described by referring to FIGS. 11 through 15. It should be understood that in the interest of clarity only one half of the instrument is being shown. In FIG. 11, the needle guide 58a has been deployed by movement of the pushrod 42 attached to the deployment link 64a. As shown in FIG. 12 and FIG. 13, the rigid shaft 50a within the hollow cylinder 54a is slidably moved and in turn pushes the flexible tubular member 56a, thereby displacing the needle carrier 84a along an arc described by the needle carrier 58a. The needle carrier 58a pushes the needle 88a carrying the suture 92a through the tissue and into the catch 78a as best shown in FIG. 13. The needle catches 78 are preferably made of thin gauge surgical grade stainless steel which allows the leaves to be flexible yet create a gripping force on the needles 88. Referring to FIG. 14, the rigid shaft 50a is retracted, and because of the retraction line 82a, the needle carrier 82a is retracted back into needle guide 58a and the flexible tubular member 56a is retracted back into the hollow cylinder 54a. As shown in FIG. 15, the pushrod 42 is retracted, by which the linkage previously described rotates the needle guide 58a back into the outer housing 32. Referring to FIG. 16, the suture application device 30 and the trocar assembly 106 are completely withdrawn from the abdominal wall 108, leaving the suture 92 in the abdominal wall 108, to be tied, completing the approximation of the wound 120.

Another embodiment of the described invention is shown in FIGS. 17, 17A, 18 and 18A. It should be understood that in the interest of clarity only one half of the instrument is being shown. The second half is a virtual copy of the first half in both function and structure. Typical materials used in this embodiment are injection molded materials such as polycarbonate, and surgical grade stainless steel.

A suture application device 126 includes an outer housing 128, with finger grips 130a and 130b, and a deployment catch 132. A deployment sleeve 134, slidably disposed within the outer housing 128, has a retention catch 136. A driver shaft 138, which is slidably disposed within the deployment sleeve 134 includes a button 140 and has a hole 142, into which is bonded an elongate rigid shaft 144. The rigid shaft 144 passes through a hole 146 in the deployment sleeve 134, through a hole 148 in an outer housing rib 150, through another hole 152 in the deployment sleeve 134 and terminates slidably disposed within a hollow cylinder 154. The hollow cylinder 154 is pivotally attached to the deployment sleeve 134 by means of a pivot pin 156 disposed on either side of the hollow cylinder 154, and inserted into holes 158 in deployment sleeve 134. An elongate flexible member 160 is also slidably disposed within the hollow cylinder 154. A needle guide assembly 162 includes: a needle guide 164, secured within the hollow cylinder 154 so as to allow the flexible member 160 to slidably transition from the hollow cylinder 154 to the curved needle guide 164; a needle 166 to which is secured a suture 168; and a needle catch 174 secured between a boss 170 and another boss 172.

Use and operation of this embodiment of the invention will be described beginning with reference to FIG. 18. The suture application device 126 is introduced into the abdomen through a trocar assembly in the same manner as described in the previous embodiment. Subsequently, a deployment arm 177 is pushed such that the retention catch 136 snaps past the deployment catch 132. Deployment sleeve 134 slides within the outer housing 128 and compresses deployment spring 176 between a wall 178 of the deployment sleeve 134 and the outer housing rib 150. The needle guide assembly 162 is forced to slide along with the deployment sleeve 134 with a cam 182 riding in a track 184, deploying the needle guide assembly as shown in FIGS. 17, 17A, 18, and 18A. Similar to the previously described embodiment, the needle 166 is driven out of the needle guide 164 by pushing the button 140, thereby pushing the rigid shaft 144, which in turn pushes the flexible member 160, which follows the curvature of needle guide 164 and pushes the needle into the catch 174. As seen in FIG. 18, the length of travel permitted button 140 is restricted by a slot 194 in driver shaft 138 sliding past a pin 192 secured to the deployment sleeve 134.

The needle guide assembly 162 is retracted back into the outer housing 128 by releasing the catch 132. The spring 176 forces the deployment sleeve 134 back to its original position, thereby causing the cam 182 to follow the track 184 such that the position of the needle guide assembly 162 is once again as shown in FIGS. 17 and 17A.

Figure 19:
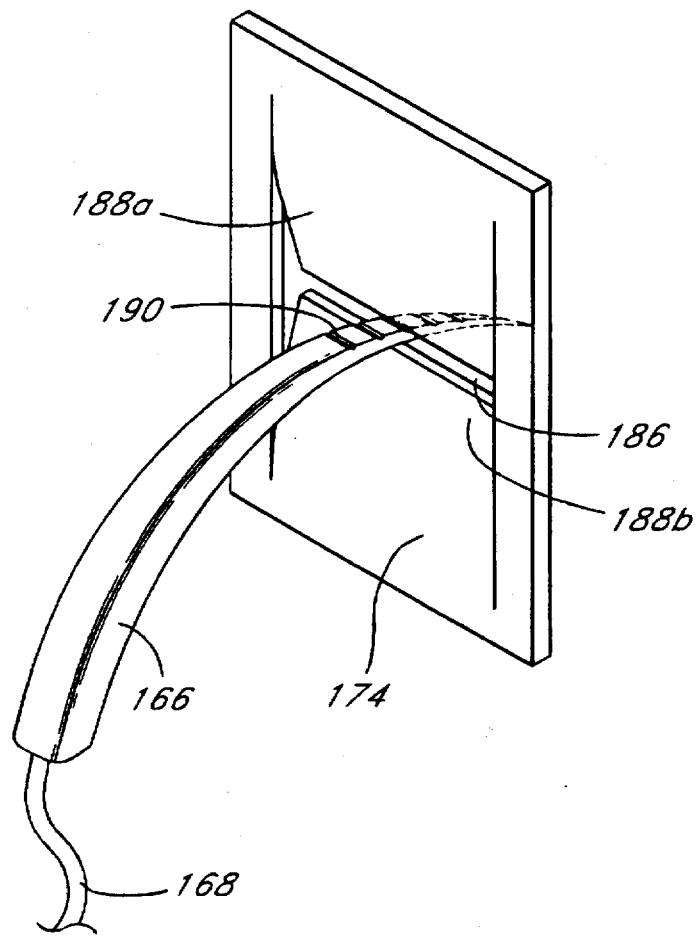
FIG. 19 is a detail perspective view of a needle showing ridges on the needle to secure the needle in the catch.

FIG. 19 shows a detail view of the needle 166 secured to the suture 168 as it enters the catch 174 through a slot 186 created by spring leaves 188a and 188b. The catch 174 is preferably made of thin gauge spring steel to allow the leaves to be flexible yet create a gripping force on the needle. Ridges 190 on needle 166 enable the catch 174 to capture and hold the needle 166. The capture and holding of the needle 166 by the catch 174 is facilitated by the spring leaves 188 being disposed to bend away from the axis of needle penetration, thus snapping into the ridges 190.

Figure 19A:
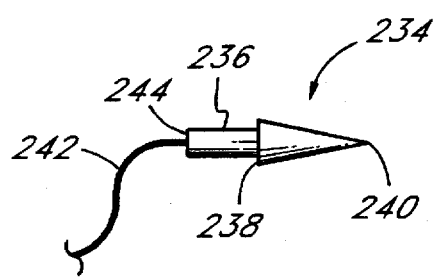
FIG. 19A is a detail plan view of an alternate needle.
Figure 19C:
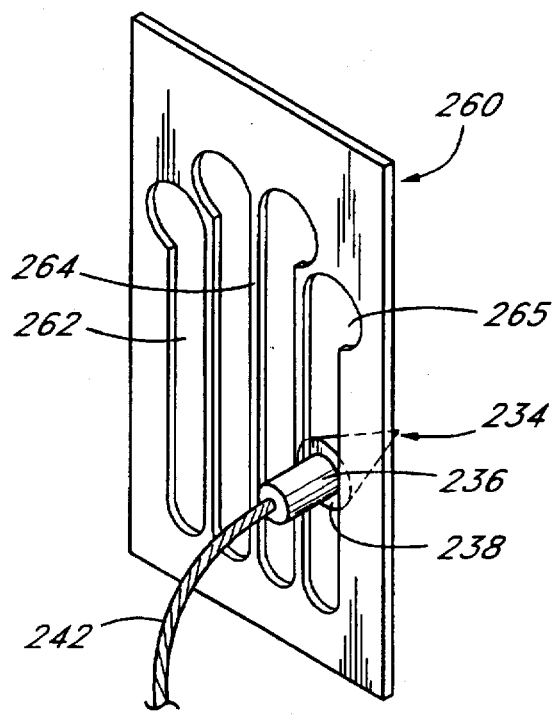
FIG. 19C is a detail perspective view of an alternate catch mechanism with a needle.
Figure 19B:
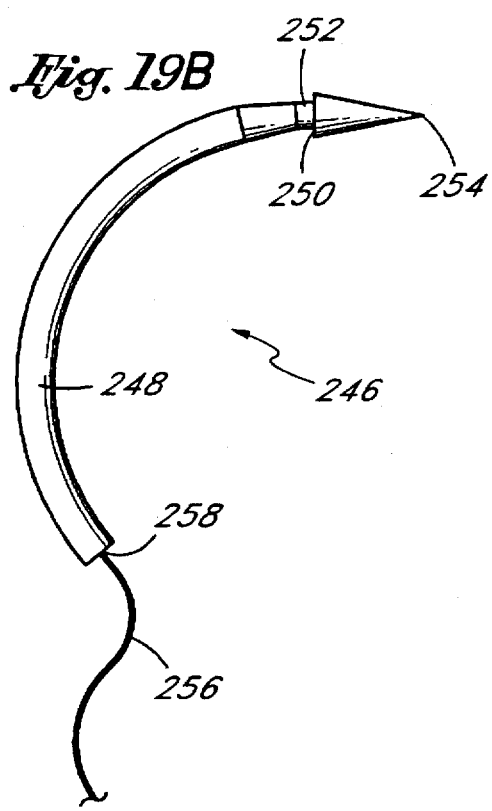
FIG. 19B is a detail plan view of another alternate needle.

FIGS. 19A through 19B show detail plan views of alternate needle embodiments. Referring to FIG. 19A, a needle 234 comprises a body 236, and a shoulder 238 tapering to a point 240. A length of suture material 242 is inserted into a hole 244 and attached to the needle 234 thereby. Referring now to FIG. 19B, a needle 246 comprises a body 248 and a shoulder 250 formed by a groove 252 which tapers to a point 254. A length of suture material 256 is inserted into a hole 258 and attached to the needle 246 thereby.

Figure 19D:
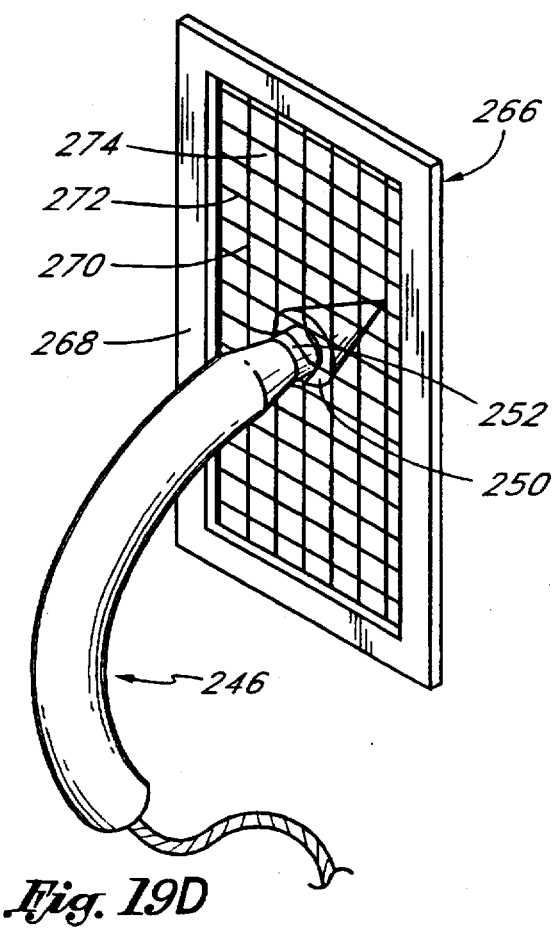
FIG. 19D is a detail perspective view of another catch mechanism with a needle.

FIGS. 19C through 19D show detail perspective views of alternate catch embodiments and illustrate their operation. A catch 260 is preferably constructed of thin stainless steel of high temper, such as ANSI 301 full hard. Referring to FIG. 19C, a catch 260 includes openings 262 defined by ribs 264. As the needle 234 enters the opening 262, the ribs 264 deflect slightly to allow the shoulder 238 to pass through. After the shoulder 238 has passed the ribs 264, the ribs spring back to their original position defining the openings 262. The openings 262 are chosen to be smaller in dimension than the shoulder 238. This causes the catch 260 to retain the needle 234 by the interference between the shoulder 238 and the ribs 264 around the body 236. When it is necessary to remove the needle 234 from the catch 260, it may be moved toward an opening 265 which is sized to allow the needle shoulder 238 to pass through without resistance.

Referring now to FIG. 19D, a catch includes a frame 268 to which is attached a woven mesh 270. Threads 272 creating the woven mesh 270 may be made out of nylon or polyester or the like woven in a common over/under pattern. The weaving of the threads 272 creates holes 274 in the mesh through which a needle 246 may be passed. The needle 246 is constructed such that the shoulder 250 defined by the groove 252 is larger than the holes 274, or conversely, the holes 274 are chosen to be smaller than the shoulder 250. The point 254 of the needle 246 pushes the threads 272 aside creating room for the shoulder 250 to pass through the holes 274. As the threads 272 return to their original positions, the catch 266 holds onto the needle 246 by means of the mismatch in the size of the holes 274 and the shoulder 250.

It may be seen and should be understood that catches 260 and 266 are capable of catching either needle 234 or 246. The examples of needle 234 coupled with catch 260 and needle 246 coupled with catch 246 are given purely to illustrate the concepts of each embodiment and do not exclude their coupling with alternate designs.

Yet another embodiment of the present invention is shown in FIGS. 20, 20A, 21, 22 and 23. It should be again understood that in the interest of clarity only one half of the instrument is being shown. The other half is quite similar in function and structure as the half described herein. The upper portion of the device is similar in construction and materials to the previously disclosed embodiments, and is not repeated here.

A suture application device 196 includes an outer housing 198 having bosses 200 into which a pin 202 is rotatably inserted. The pin 202 is secured to an arm 204, which is attached to a needle carrier 206. A pin 208 on needle carrier 206 is rotatably inserted into a hole 210 in a link 212. Another pin 214 is secured to a pushrod 216 and is rotatably inserted into another hole 218 in the link 212. The pushrod 216 is attached to a sleeve 220 slidably disposed within the outer housing 198.

FIG. 20A shows a detail view of a needle 222 held in a recess 224 in the needle carrier 206. A suture 226 is attached to the needle 222 and is threaded through a slot 228 in the needle carrier 206. All components in this mechanism are preferably constructed of surgical grade stainless steel, chosen for its biocompatibility and strength.

Use and operation of this embodiment of the invention will be described beginning with reference to FIG. 20. The suture application device 196 is introduced into the abdomen through a trocar assembly in the same manner as described in a previous embodiment. Sleeve 220 slides within the housing 198 in the direction indicated by the arrow. As shown in FIG. 21, as the sleeve 220 moves, it pushes the pushrod 216 which causes the link 212 to cause the needle carrier 206, along with the needle 222 and the suture 226, to rotate about the axis defined by the pin 202. Referring to FIG. 22, it may be seen that the needle 222 is driven into a catch 230 through an opening 232 in the outer housing 198. Accordingly, in reference to FIG. 23, it is seen that as the pushrod 216 is retracted, the link 212 is also retracted, causing the needle carrier 206 to rotate about the pivot pin 202 and back through the opening 232 into the outer housing 198, the same position as shown in FIG. 20.

Figure 24:
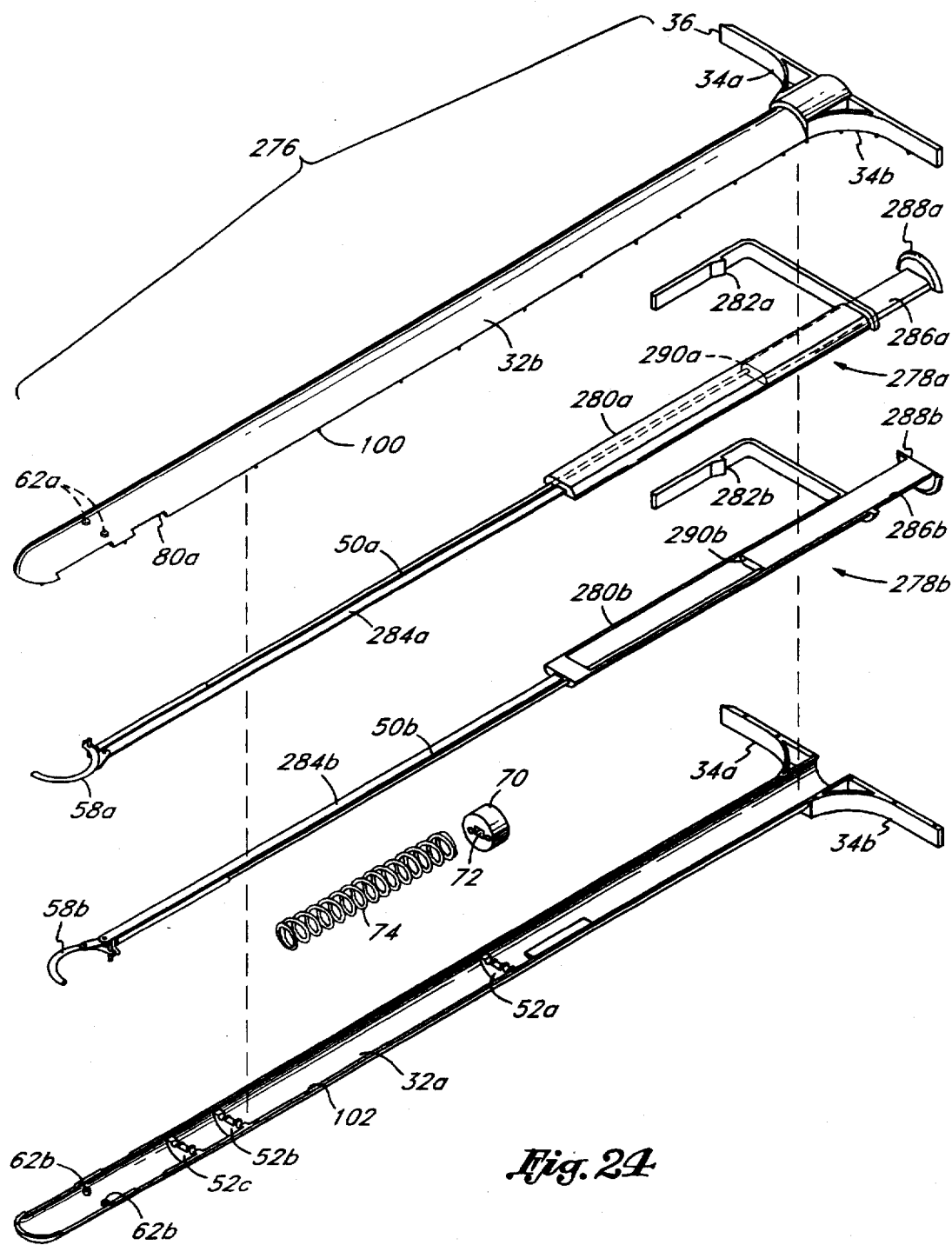
FIG. 24 is a exploded perspective view of an alternate embodiment of the present invention which allows each of the guide tracks to be actuated independently.

Another embodiment of the present invention is described in FIGS. 24, 24A, 24B, 24C, and 24D. FIG. 24, shows an exploded perspective view of a suture device which is similar in construction to the previously described suture application device 30 and includes an outer housing 32, comprised of two halves 32a and 32b, with finger grips 34a and 34b, and a deployment catch 36. Residing within the outer housing 32, are independent needle driver assemblies 278a and 278b. For purposes of discussion, only one of the needle driver assemblies 278 will be described, although it should be understood that both are substantially identical in structure and function.

A deployment sleeve 280a, slidably disposed within the outer housing 32, has a retention catch 282a and is attached to a pushrod 284a, constructed for example, of stainless steel. A driver shaft 286a includes a button 288a and has a hole 290a, into which is bonded an elongate rigid shaft 50a. The rigid shaft 50a, which may be made of music wire, passes through outer housing ribs 52a, 52b and 52c. In construction similar to and as best shown in FIG. 4A, the rigid shaft 50a terminates slidably disposed within the hollow cylinder 54a, which is held in recesses in the outer housing ribs 52b and 52c. Elongate flexible tubular member 56a, that may be made of polypropylene or other suitable material, is also slidably disposed within the hollow cylinder 54a. As shown in FIG. 6, needle guide 58a may also be constructed from stainless hypodermic tubing, and has pivot pins 60a and 60b pivotally disposed within outer housing bosses 62a and 62b. A driving link 64a is attached by a link pin 66 to the pushrod 42 (284a in FIG. 24) and to the needle guide 58a by a pivot pin 68a, with the entire mechanism preferably made of stainless steel so as to maximize the biocompatibility as well as the strength of the actuating members. It may be appreciated from FIG. 24 that, as described, there are two needle guides 58a and 58b oppositionally disposed within the outer housing 32.

Referring again to FIG. 24, driver retainer 70 is slidably disposed within the outer housing 32, and is fixably attached to rigid shafts 50a and 50b, with a hole 72 to allow the pushrod 284a to pass slidably therethrough. Driver spring 74, preferably wound from stainless steel wire is compressed between the driver retainer 70 and the outer housing rib 52b.

It may be appreciated by the foregoing that the needle driver assemblies 278a and 278b may be actuated independently. The internal mechanisms and components are similar in construction to the embodiment described in FIG. 1A through 1H.

Figures 24A, 24B:
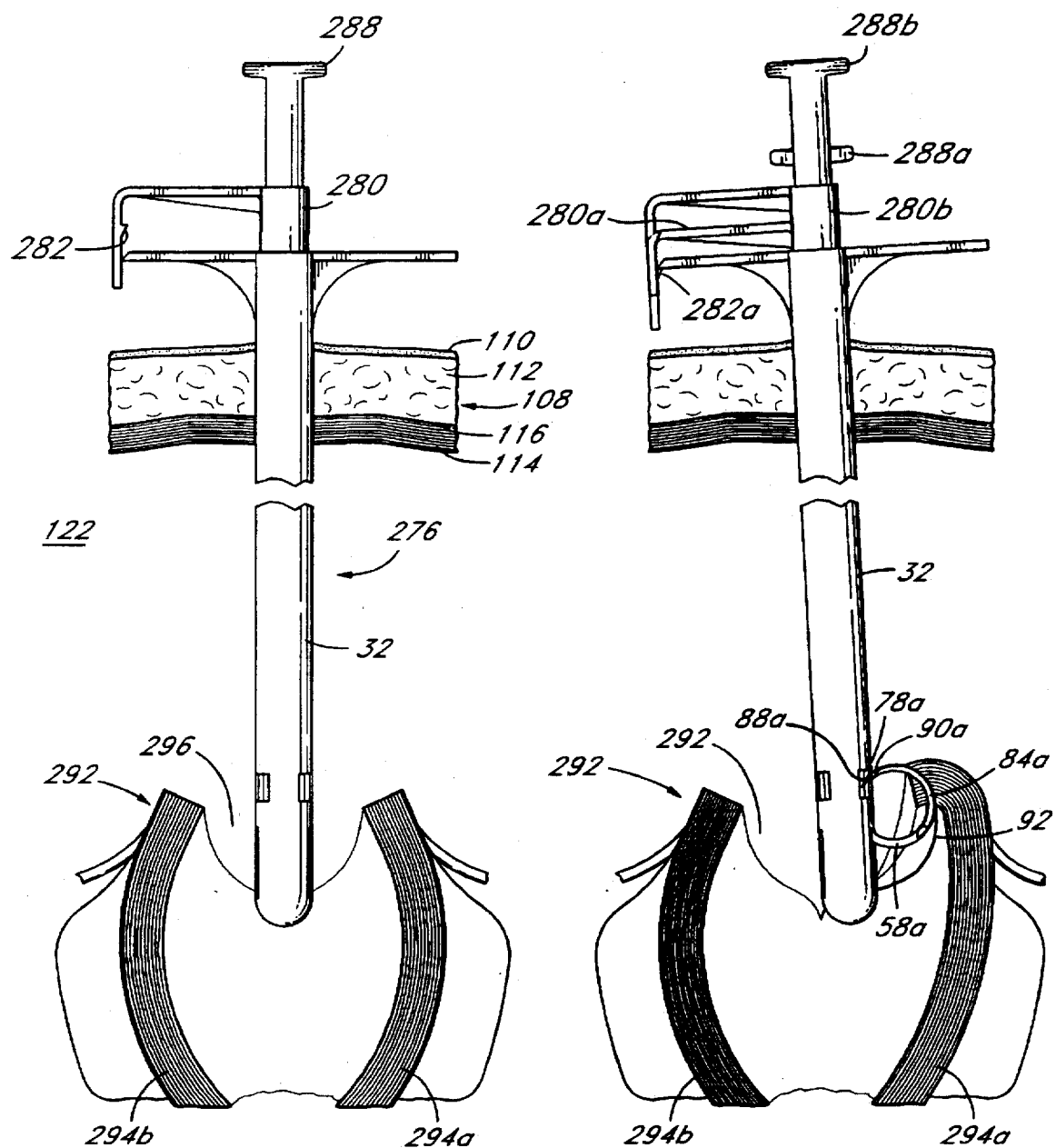
FIGS. 24A through 24D illustrate the general operation of the independent guide deployment.
Figures 24C, 24D:
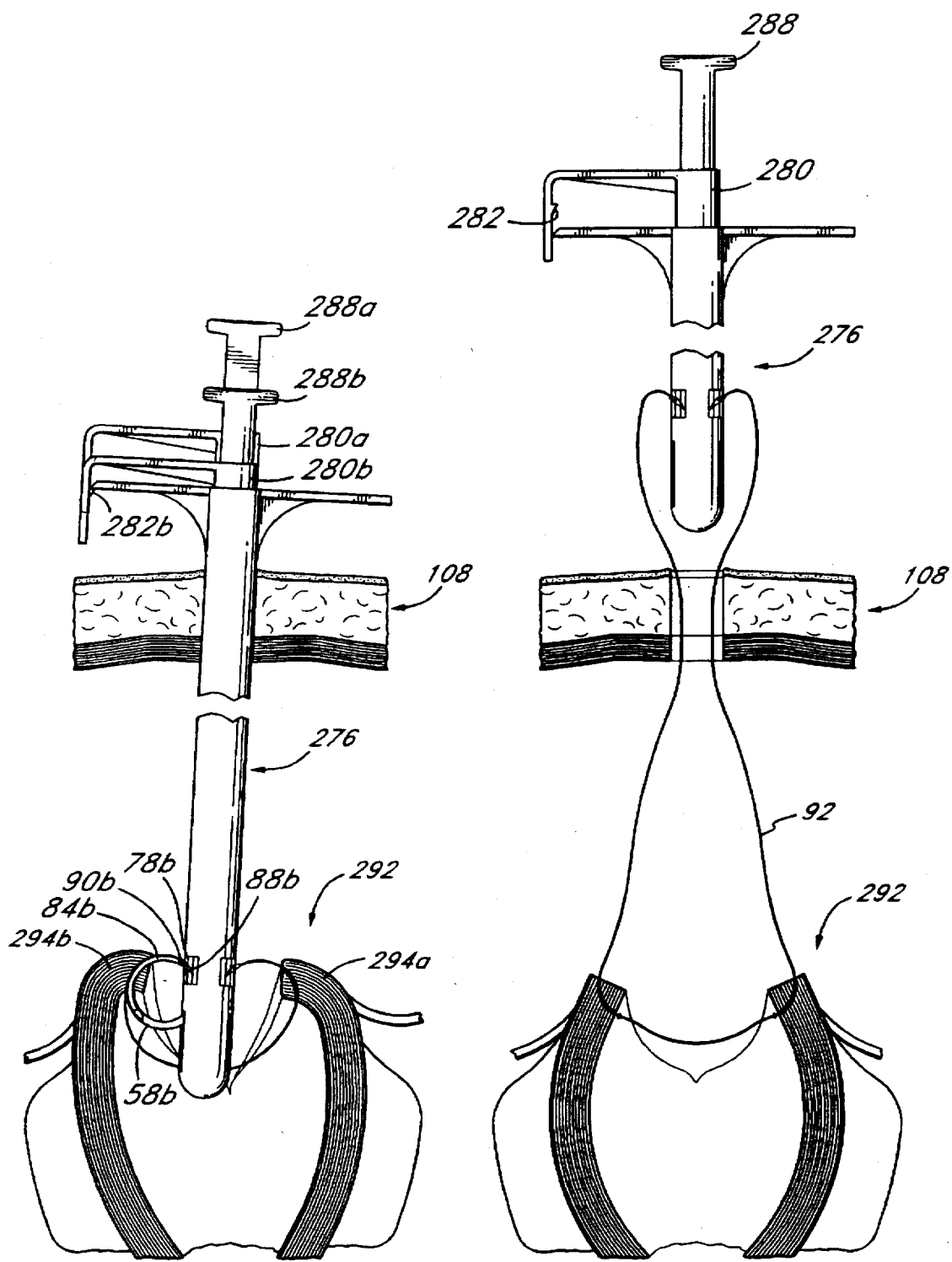

FIGS. 24A through 24D illustrate the use and operation of this embodiment of the invention. The use of this embodiment will be described beginning with reference to FIG. 24A which shows a suture device 276 inserted through the abdominal wall 108, which includes a layer of skin 110, a fat layer 112, a muscle layer 114 and a fascial layer 116. Within the abdominal cavity 122 lies a hollow organ 292, which may be, for example, a uterus. The organ includes walls 294 into which an opening 296 has been made. The opening 296 would generally have been created by a surgeon using traditional surgical tools such as a scalpel or scissors, and may have been made in order to excise a fibroid tumor or the like. The suture device 276 is inserted into the opening 296. Referring to FIG. 24B, the deployment sleeve 280a is depressed, rotating the needle guide 58a outside the bounds of the housing 32. The deployment sleeve 280a is locked down by deployment catch 282a. The needle 88a is attached to the suture material 92, and rests in the recess 90a in the needle carrier 84a (also see FIG. 6 for a more detailed view). Needle driver button 288a is depressed, driving the needle carrier 84a holding the needle 88a through the organ wall 294a and into the needle catch 78a. The needle driver button 288a is returned to its original position, and the deployment sleeve 280a retracted, leaving the suture 92 placed through one wall 294a of the hollow organ 292 utilizing needle driver assembly 278a. FIG. 24C illustrates a similar process on the opposing wall 294b of the hollow organ 292 utilizing needle driver assembly 278b. Referring to FIG. 24D, it can be seen that the suture 92 is withdrawn through the abdominal wall where the suture 92 is cut away from the suture device 276. A knot is then tied in the suture 92 to approximate the walls 294 of the hollow organ 292, and additional sutures 92 are placed as necessary.

Other embodiments of the present invention comprise modifications of the above embodiments which include a single needle driver, either with or without a catch system. The single needle driver embodiments perform the same function as the dual needle driver embodiments described herein, with minor operational modifications. For example, the single needle driver embodiments require that the suture application device be removed from the body cavity to load the second needle. In some applications, however, this is not a severe operational limitation, and single sided needle drivers or suturing devices should be understood to be contemplated in addition to the above described dual needle embodiments.

In some applications, such as for the placement of sutures for suspension of the bladder for the treatment of female incontinence, it may be desirable to use a single sided device. This is due to the limited space for deployment and visualization of the instrument. For bladder suspension, the device may be used as follows. After loading a semi-circular needle similar to that shown in FIG. 19B into a single guiding track, the suture application device is introduced into the body cavity via a surgical trocar, and a suture is driven into the vaginal wall just below the urinary bladder neck. The suture application device is manipulated to catch the needle, and the device withdrawn from the body cavity carrying the needle and suture. The opposite end of the suture, which also has an attached needle, is then loaded into the suture application device, and introduced back into the body cavity. This needle is driven through one side of Cooper's ligament, and again the device withdrawn from the body. The surgeon may then repeat the same sequence, driving through the opposite side of Cooper's ligament. The surgeon may then tie the sutures at his discretion, placing the proper amount of tension on the sutures to effect the suspension of the bladder.

A similar sequence may be contemplated for use in other applications such as the previously mentioned closure of a body organ, or of the fascial puncture wounds. It may also be contemplated for use in the placement of gastrostomy tubes, or in the approximation of tissue flaps such as that accomplished in gastric fundoplication.

Figure 25:
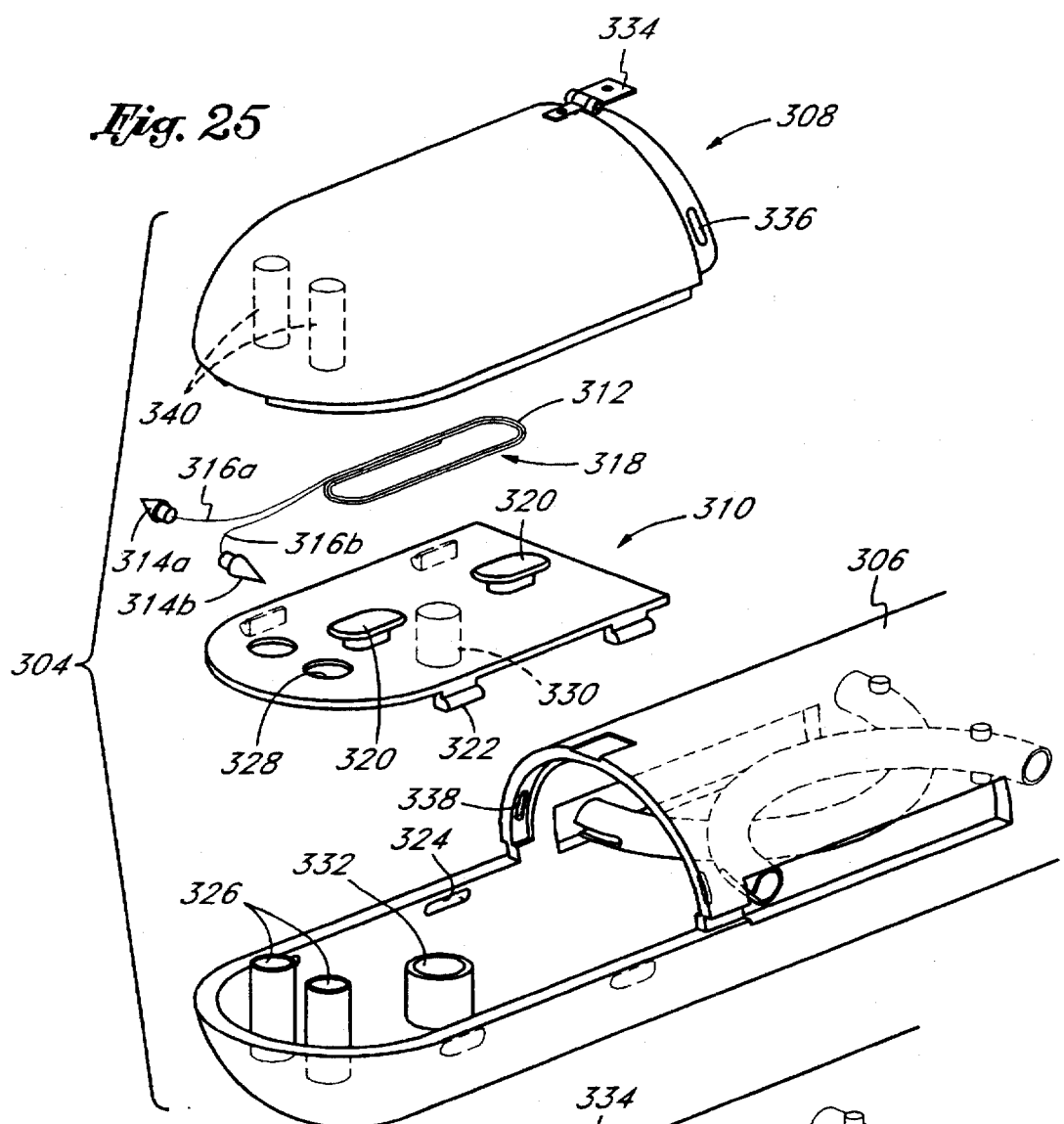
FIG. 25 is an exploded perspective view of the general structure of a suture loading system.
Figure 26:
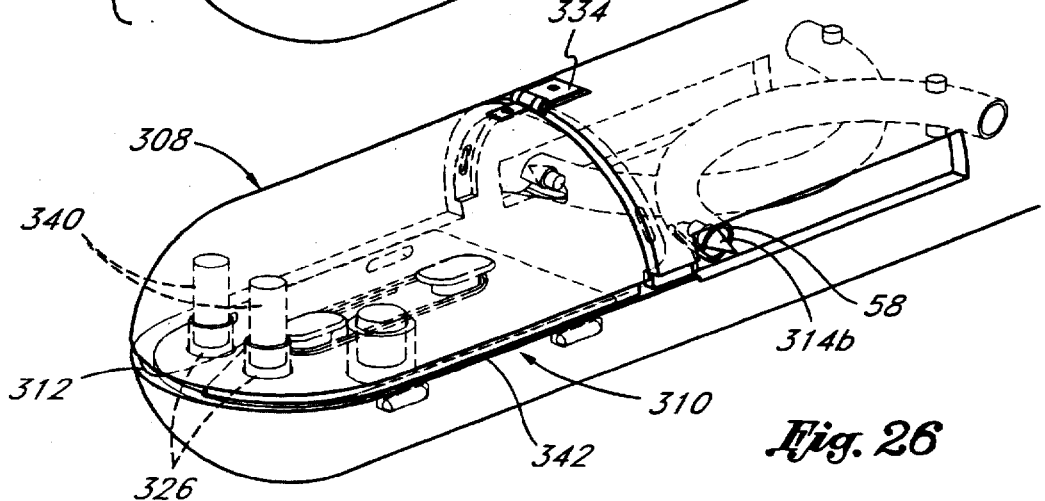
FIG. 26 is a perspective view of the assembly described in FIG. 25

Referring now to FIG. 25, there may be seen the tip of a suture application device 304 which includes a cannular body 306, a hinged tip 308 and a suture carrier plate 310. The suture carrier plate 310 may be molded from polyethylene or other suitable material which may be adapted for the "bone dry" sterilization process previously described. A piece of suture material 312 has needles 314a and 314b, which as before are preferably constructed from surgical grade stainless steel, attached to each end 316 to form a suture 318. The suture 318 is wound to fit over pegs 320 on the suture plate 310. Tabs 322 are molded into the plate 310 and are constructed to fit into recesses 324 molded or otherwise placed in the walls of the cannular body 306. Hollow posts 326 formed in the cannular body 306 are sized appropriately to fit snugly into holes 328, and post 330 is concomitantly sized to fit into hole 332 and along with the tabs 322 and the recesses 324, provide guidance and retention of the plate 310 within the cannular body 306. As may be seen by referring to FIGS. 25 and 26, when the hinged tip 308 is pivoted about a hinge 334, projections 336 are made to fit into recesses 338 in the cannular body 306 simultaneously causing posts 340 to mate with the hollow posts 326. The suture material 312 is guided in channels 342 on each side of the cannular body 306, and the needles 314 are loaded within the needle guides 58.

An example of an embodiment of a needle loading system is shown in FIG. 27 and includes a cannular body 344 and a needle loader 346. The needle loader 346 includes two arms 348a and 348b which terminate in needle recesses 350a and 350b, respectively, and are commonly attached to crossbar 352. FIGS. 28A through 28C are detail cross section plan views which illustrate and describe the operation of the needle loader. As may be seen in FIG. 28A, the needle recess 350 attached to the arm 348 contains a needle 354 to which is attached a piece of suture material 356. The needle 354 is held within the recess 350 by fingers 358. The fingers 358 are bent inward such that a deflective force causes them to hold the needle by shank 360, butting up against shoulder 362. Referring now to FIG. 28B, it may be seen that as the needle recess 350 is moved in the direction indicated by the arrows, the fingers 358 are deflected even further by needle guide 364 causing the fingers 358 to release the needle shank 360 and clear the needle shoulder 362. This movement forces the needle shank 360 to slide into slot 366 in needle carrier 368, as best shown in FIG. 28C. Referring back to FIG. 27, it may be seen that the force indicated by the arrows in FIGS. 28A and 28B may be provided by a thumb 370 and finger 372. It may be clearly seen that the suture carrier plate 310 may be loaded into the cannular body 344 as previously described in reference to FIGS. 25 and 26.

Figure 29:
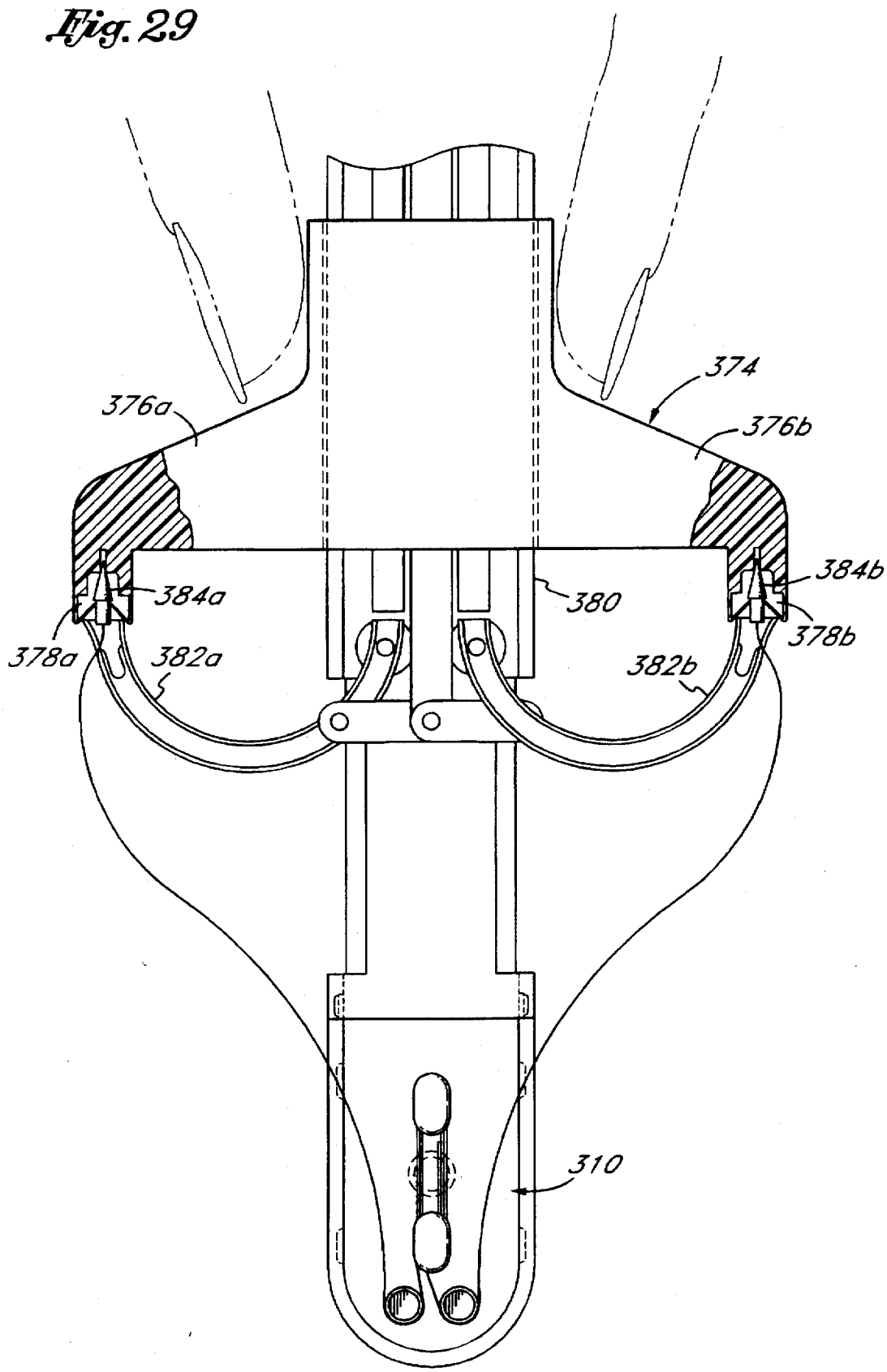
FIG. 29 is a detail cross sectional plan view of an alternate embodiment of a suture loading system.

An alternate embodiment of the needle loading system is shown in FIG. 29 wherein a needle loader 374 includes arms 376a and 376b and needle recesses 378a and 378b. As may be clearly seen, the needle recesses 378 are similar in construction and operation to those described in FIGS. 28A through 28C. However, in this embodiment, the needle loader 374 is constrained to glide along cannular body 380, aligning recesses 378 with needle guides 382, and subsequently loading needles 384 as previously outlined. As before, it may be clearly seen that the suture carrier plate 310 may be loaded into the cannular body 380 as previously described in FIG. 25 and FIG. 26.

Figure 30:
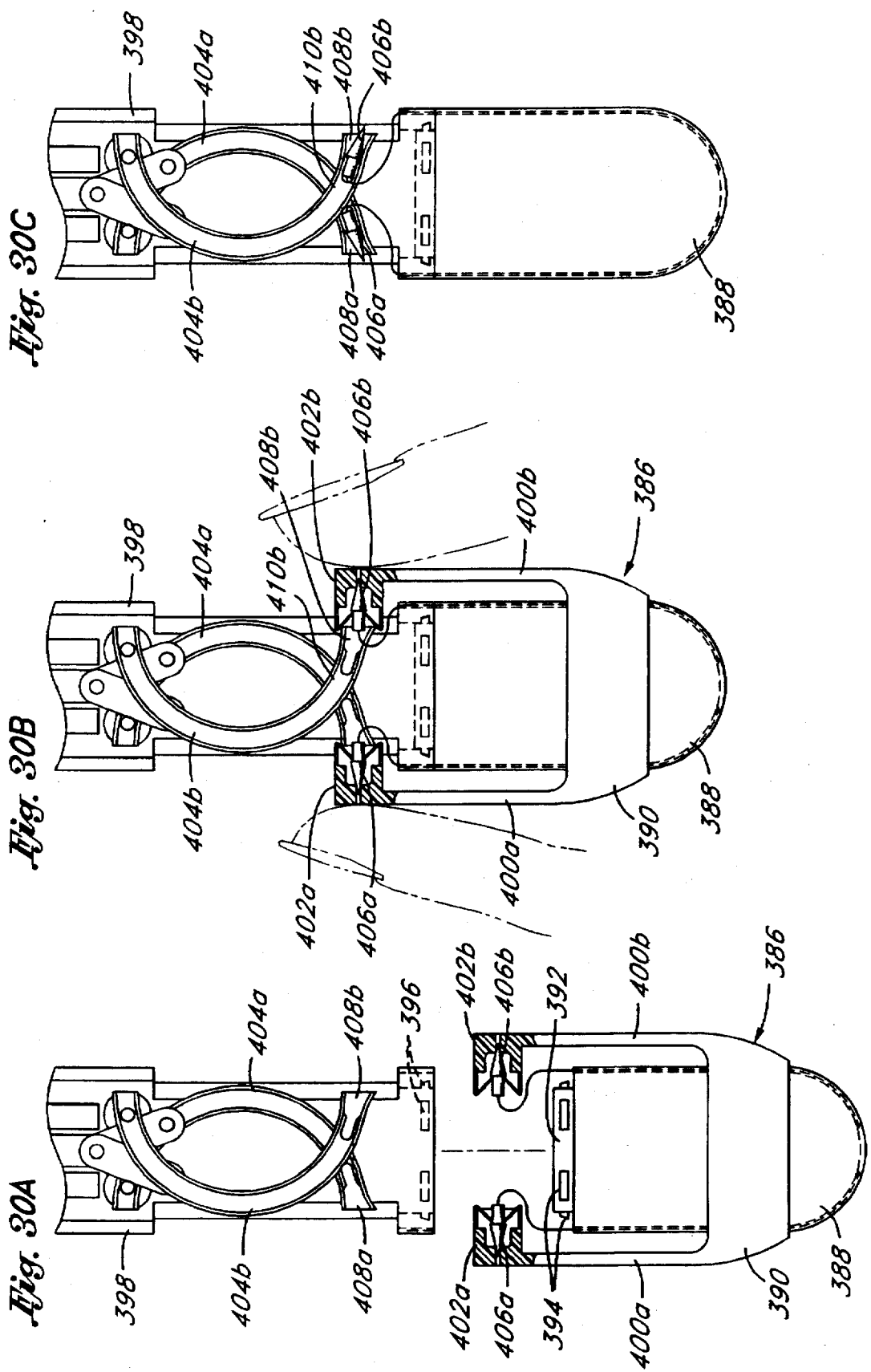
FIGS. 30A through 30C are detail cross sectional plan views of an alternate embodiment which illustrate the insertion of the needles into the needle carriers.

FIGS. 30A through 30C are detail section views which describe yet another embodiment of a needle loading system 386 which includes a cartridge 388 and a needle loader 390. The cartridge 388 is preferably molded out of polycarbonate or the like, and includes a flange 392 on which are projections 394 which are sized and designed to fit into recesses 396 in the cannular body 398. The needle loader 386 which is preferably molded out of a malleable plastic such as polypropylene, includes arms 400a and 400b and needle recesses 402a and 402b. As may be clearly seen, the needle recesses 402 are similar in construction and operation to those described in FIGS. 28A through 28C. In this embodiment, and as shown in FIG. 30B, the needle loader 386 is constrained to be engaged with the cartridge 388. As the flange 392 is snapped into the cannular body 398, projections 394 are engaged into recesses 396, aligning the needle recesses 402a and 402b with needle guides 404a and 404b, respectively. Referring now to FIGS. 30B and 30C, it may be clearly seen that by squeezing the needle recesses 402 and deflecting arms 400, the needles 406 are loaded into openings 408 in the needle guides 404 and subsequently into needle carriers 410 as previously outlined in FIGS. 28A through 28C. FIG. 30C shows that the needle loader 386 has been removed from the cartridge 388 leaving the needles 406 loaded and ready for use.

Figure 31:
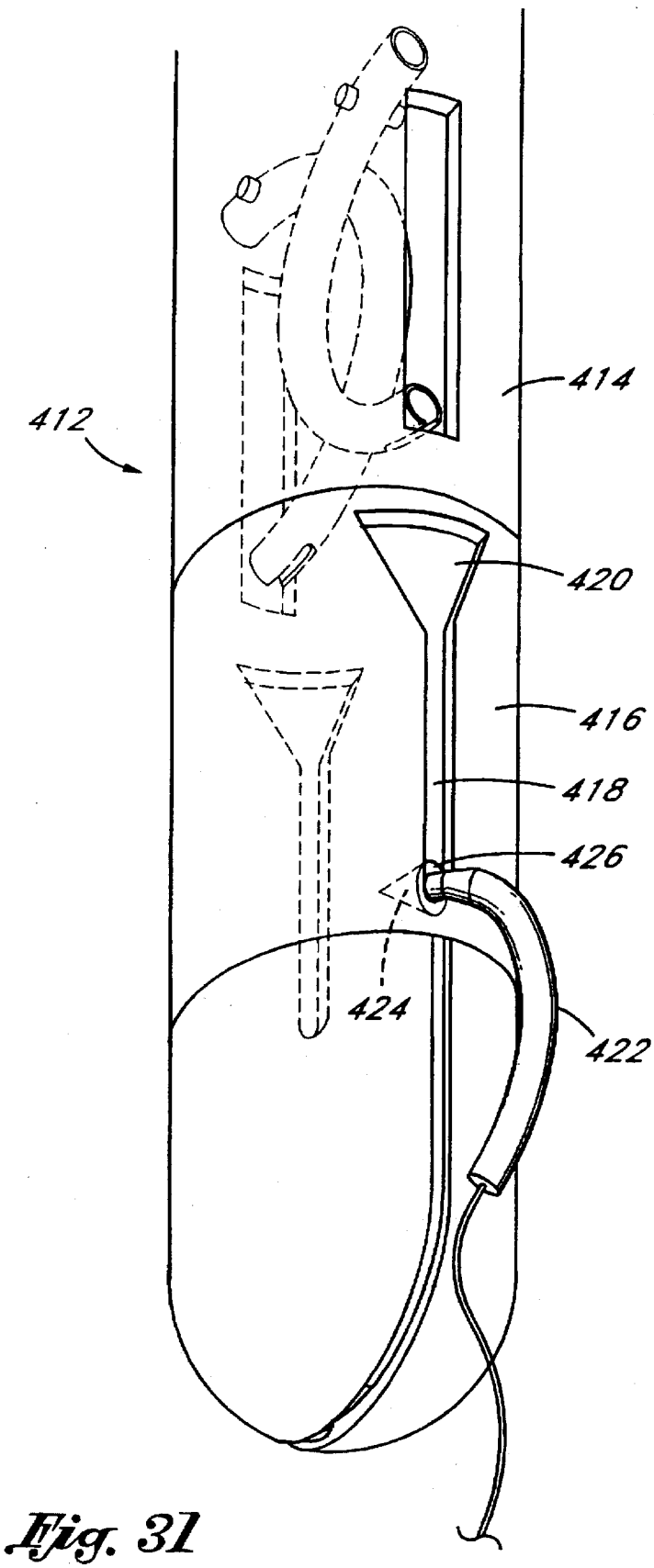
FIG. 31 is a detail perspective view of an alternate embodiment of the present invention for a suture application device which includes a cannular body and a keyhole shape needle catch.

Referring now to FIG. 31, there may be seen a detail perspective view of a suture application device 412 which includes a cannular body 414 and a needle catch 416. The needle catch 416 includes slots 418 and openings 420. Needle 422 includes a point 424 and a shoulder 426. The needle catch 416 is designed such that the openings 420 are large enough for the point 424 and the shoulder 426 of the needle 422 may easily pass through. After the needle 422 has been driven into tissue, the suture application device 412 may be manipulated to allow the point 424 and the shoulder 426 of the needle 422 to enter the opening 420. The suture application device 412 may then be moved to allow the shoulder 426 to slide down in the slot 418 which is sized such that the shoulder 426 may not pass through. Thus the needle 422 may be captured selectively at the discretion of the user.

It may also be desirable to have an interlock assembly to prevent the user of these devices from improper sequencing of the controls. It is necessary for the needle guides previously described to be deployed prior to the needle driver control being activated. Improper sequencing may cause a malfunction of the device. We therefore now describe an interlock system which prevents improper control sequencing.

Referring to FIG. 32A, a sectional detail plan view of a suture device interlock assembly 430 which includes a needle driver button 432 attached to a shaft 434 which is slidably disposed within a guide deployment sleeve 436. The guide deployment sleeve 436 includes a button 438 and a hollow shaft 440 with keyhole slot 442 and is slidably disposed within outer housing 444. Residing on the inside diameter of hollow shaft 440 is a housing 446 dimensioned to allow the shaft 434 to move slidably within it's inside diameter. At the end of the shaft 434 is a recess 448 in which sits a bent wire 450. The housing 446 is ultimately attached to the previously described pushrod 42 (see FIG. 6), and the bent wire 450 is attached to the previously described flexible members 56a, 56b (FIG. 6). The outer housing 444 contains a pocket 452 in which is slidably disposed a lockout pawl 454 which is forced by spring 456 to ride up into notch 458 in the shaft 434.

Referring now to FIG. 33, which is a detail perspective view of the lockout pawl 454 and the hollow shaft 440, it may be seen that the lockout pawl 454 has a head 460 which has a dimension larger than a smaller slot section 462 of the keyhole slot 442. This dimensional difference restrains the head 460 from passing down through the smaller slot section 462, thereby preventing the needle driver button 432 from being depressed.

Moving to FIG. 32B, it may be seen that as the button 438 is depressed, the keyhole slot 442 moves relative to the lockout pawl 454. As previously described in other embodiments, this movement of button 438 deploys the needle guides. Referring back to FIG. 33, it may be seen that the larger slot section 464 of the keyhole slot 442 is moved into a position which aligns the lockout pawl 454 with the larger slot section 464. As may be seen in FIG. 32C, as the needle driver button 432 is depressed, the lockout pawl 454 is driven back into the pocket 452 against the tension of the spring 456 as the notch 458 in the shaft 434 moves away from the lockout pawl 454. As previously described in other embodiments, this movement of needle driver button 432 drives the needle or needles through tissue. It should be noted that as the lockout pawl 454 drops into the larger slot section 464, it effectively prevents the movement of the hollow shaft 440. This has the effect of locking the needle guides in the deployed position during the driving of the needles. It also should be understood that the reverse movements of the controls will return the buttons to their original positions as described in FIG. 32A.

It will be understood that the apparatus and method of the present invention for an endoscopic suture system may be employed in numerous specific embodiments in addition to those described herein. Thus, these numerous other embodiments of the invention, which will be obvious to one skilled in the art, including but not limited to changes in the dimensions of the device, the type of materials employed, the location and type of needles, driving mechanisms, catching mechanisms, needle loading mechanisms, etc., are to be included within the scope of the present invention. The apparatus and method of the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

We claim:

1. A suture device comprising:

an elongate cannular body member having a longitudinal axis and an internal chamber with a first lateral exit port near a distal end of said elongate cannular body member;

a first actuator located near a proximal end of said elongate cannular body member and extending into said internal chamber, said first actuator having a retracted position and a deployed position; and a first needle deployment mechanism comprising a first needle carrier pivotally mounted within said internal chamber near said distal end of said elongate cannular body member, said first needle deployment mechanism connected to said first actuator and having a retracted configuration when said first actuator is in said retracted position wherein substantially all of said first needle deployment mechanism is contained within said internal chamber and a deployed configuration when said first actuator is in said deployed position, said first needle deployment mechanism includes means for transporting said first needle carrier outside of said internal chamber through said first lateral exit port along a path having an initial direction away from said elongate cannular body member longitudinal axis as said first actuator begins to move from said retracted position toward said deployed position followed by a direction toward said elongate cannular body member longitudinal axis as said first actuator approaches said deployed position.

2. A suture device as defined in claim 1 further comprising:

a needle having a suture attachment point inserted in said first needle carrier;

a suture attached to said needle suture attachment point; and a needle capture system located on said elongate cannular body member at a location which intercepts said portion of said first needle carrier path which approaches toward said elongate cannular body member.

3. A suture device as defined in claim 1 further comprising:

a second actuator located near said proximal end of said elongate cannular body member and extending into said internal chamber, said second actuator having a retracted position and a deployed position; and a second needle deployment mechanism comprising a second needle carrier pivotally mounted within said internal chamber near said distal end of said elongate cannular body member, said second needle deployment mechanism connected to said second actuator and having a retracted configuration when said second actuator is in said retracted position wherein substantially all of said second needle deployment mechanism is contained within said internal chamber and a deployed configuration when said second actuator is in said deployed position, said second needle deployment mechanism includes means for transporting said second needle carrier outside of said internal chamber through a second lateral exit port along a path having an initial direction away from said elongate cannular body member longitudinal axis as said second actuator begins to move from said retracted position toward said deployed position followed by a direction toward said elongate cannular body member longitudinal axis as said second actuator approaches said deployed position.

4. A suture device as defined in claim 3 further comprising a link which connects said first actuator with said second actuator such that said second needle deployment mechanism is deployed simultaneously with said first needle deployment mechanism by either one of said first actuator or said second actuator, wherein said first and second needle deployment mechanisms are deployed on opposite sides of said elongate cannular body member.

5. A suture device as defined in claim 3 wherein said first actuator comprises a first sub-actuator and a second sub-actuator, each having a retracted position and a deployed position which is independent of the other, said first needle deployment mechanism includes means for transporting said first needle carrier outside of said internal chamber along said path having an initial direction away from said elongate cannular body member as said first sub-actuator moves from said retracted position toward said deployed position followed by said direction toward said elongate cannular body member as said second sub-actuator moves from said retracted position toward said deployed position.

6. A suture device comprising:

an elongate cannular body member which defines an internal chamber;

a first actuator located near a proximal end of said elongate cannular body member and extending into said internal chamber, said first actuator having a retracted position and a deployed position;

a first needle deployment mechanism comprising a first needle carrier pivotally mounted within said internal chamber near a distal end of said elongate cannular body member, said first needle deployment mechanism connected to said first actuator and having a retracted configuration when said first actuator is in said retracted position wherein substantially all of said first needle deployment mechanism is contained within said internal chamber and a deployed configuration when said first actuator is in said deployed position, said first needle deployment mechanism includes means for transporting said first needle carrier outside of said internal chamber along a path having an initial direction away from said elongate cannular body member as said first actuator begins to move from said retracted position toward said deployed position followed by a direction toward said elongate cannular body member as said first actuator approaches said deployed position;

a second actuator located near said proximal end of said elongate cannular body member and extending into said internal chamber, said second actuator having a retracted position and a deployed position; and a second needle deployment mechanism comprising a second needle carrier pivotally mounted within said internal chamber near said distal end of said elongate cannular body member, said second needle deployment mechanism connected to said second actuator and having a retracted configuration when said second actuator is in said retracted position wherein substantially all of said second needle deployment mechanism is contained within said internal chamber and a deployed configuration when said second actuator is in said deployed position, said second needle deployment mechanism includes means for transporting said second needle carrier outside of said internal chamber along a path having an initial direction away from said elongate cannular body member as said second actuator begins to move from said retracted position toward said deployed position followed by a direction toward said elongate cannular body member as said second actuator approaches said deployed position.

7. A suture device as defined in claim 6 further comprising a link which connects said first actuator with said second actuator such that said second needle deployment mechanism is deployed simultaneously with said first needle deployment mechanism by either one of said first actuator or said second actuator, wherein said first and second needle deployment mechanisms are deployed on opposite sides of said elongate cannular body member.

8. A suture device as defined in claim 6 wherein said first actuator comprises a first sub-actuator and a second sub-actuator, each having a retracted position and a deployed position which is independent of the other, said first needle deployment mechanism includes means for transporting said needle carrier outside of said internal chamber along said path having an initial direction away from said elongate cannular body member as said first sub-actuator moves from said retracted position toward said deployed position followed by said direction toward said elongate cannular body member as said second sub-actuator moves from said retracted position toward said deployed position.

9. A suture device as defined in claim 6 further comprising:

a needle having a suture attachment point inserted in said first needle carrier;

a suture attached to said needle suture attachment point; and a needle capture system located on said elongate cannular body member at a location which intercepts said portion of said first needle carrier path which approaches toward said elongate cannular body member.

* * * * *